US008579955B2

(12) United States Patent
Schwartz et al.

(10) Patent No.: US 8,579,955 B2
(45) Date of Patent: Nov. 12, 2013

(54) ANTI-ARRHYTHMIA DEVICES AND METHODS OF USE

(75) Inventors: Robert S. Schwartz, Rochester, MN (US); Robert A. Van Tassel, Excelsior, MN (US); David R. Holmes, Jr., Rochester, MN (US)

(73) Assignee: Syntach AG, Schaffhausen (CH)

( * ) Notice: Subject to any disclaimer, the term of this patent is extended or adjusted under 35 U.S.C. 154(b) by 1351 days.

(21) Appl. No.: 11/551,670

(22) Filed: Oct. 20, 2006

(65) Prior Publication Data
US 2007/0049866 A1  Mar. 1, 2007

Related U.S. Application Data

(63) Continuation of application No. 10/192,402, filed on Jul. 8, 2002, now abandoned.

(60) Provisional application No. 60/303,573, filed on Jul. 6, 2001.

(51) Int. Cl.
*A61F 2/82* (2013.01)

(52) U.S. Cl.
USPC ......... 623/1.11; 623/1.14; 623/2.38; 128/898

(58) Field of Classification Search
USPC ......................................... 623/1.11; 128/898
See application file for complete search history.

(56) References Cited

U.S. PATENT DOCUMENTS

| 4,580,568 A | 4/1986 | Gianturco |
| 5,176,135 A | 1/1993 | Fain et al. |
| 5,234,448 A | 8/1993 | Wholey et al. |
| 5,254,127 A | 10/1993 | Wholey et al. |
| 5,312,456 A | 5/1994 | Reed et al. |
| 5,360,440 A | 11/1994 | Andersen |
| 5,423,851 A | 6/1995 | Samuels |
| 5,507,779 A | 4/1996 | Altman |
| 5,509,924 A | 4/1996 | Paspa et al. |
| 5,531,779 A | 7/1996 | Dahl et al. |

(Continued)

FOREIGN PATENT DOCUMENTS

| EP | 0 497 620 A2 | 8/1992 |
| EP | 0 558 352 A1 | 9/1993 |

(Continued)

OTHER PUBLICATIONS

The Thoracic and Cardiovascular Surgeon, III Supplement, vol. 47, Aug. 1999, pp. 347-351, "*An Anatomic Approach to Prevention of Atrial Fibrillation: Pulmonary Vein Isolation With Through-The-Balloon Ultrasound Ablation (TTB-USA)*".

(Continued)

*Primary Examiner* — Thomas J Sweet
*Assistant Examiner* — Christopher D Prone
(74) *Attorney, Agent, or Firm* — Inskeep IP Group, Inc.

(57) ABSTRACT

An apparatus and method of use are disclosed for treating, preventing and terminating arrhythmias. In particular, the apparatus is implantable within or on various tissues and structures and is used to prevent or block conduction of aberrant impulses. A variety of methods of the present invention may be used to attack arrhythmias by short-circuiting impulses, inducing fibrosis, ablating tissue or inducing inflammation. In addition, the device and methods may also be used to treat aneurysms. The device may also be used to treat hypertension, and to function as a blood pressure regulator.

8 Claims, 21 Drawing Sheets

(56) References Cited

U.S. PATENT DOCUMENTS

| | | |
|---|---|---|
| 5,545,183 A | 8/1996 | Altman |
| 5,551,426 A | 9/1996 | Hummel et al. |
| 5,551,427 A | 9/1996 | Altman |
| 5,569,272 A | 10/1996 | Reed et al. |
| 5,584,879 A | 12/1996 | Reimold et al. |
| 5,618,310 A | 4/1997 | Ger et al. |
| 5,649,906 A | 7/1997 | Gory et al. |
| 5,658,327 A | 8/1997 | Altman et al. |
| 5,662,698 A | 9/1997 | Altman et al. |
| 5,674,272 A | 10/1997 | Bush et al. |
| 5,676,850 A | 10/1997 | Reed et al. |
| 5,713,863 A | 2/1998 | Vigil et al. |
| 5,725,567 A | 3/1998 | Wolff et al. |
| 5,749,890 A | 5/1998 | Shaknovich |
| 5,769,883 A | 6/1998 | Buscemi et al. |
| 5,824,030 A | 10/1998 | Yang et al. |
| 5,837,007 A | 11/1998 | Altman et al. |
| 5,843,169 A | 12/1998 | Taheri |
| 5,891,108 A | 4/1999 | Leone et al. |
| 5,899,917 A | 5/1999 | Edwards et al. |
| 5,910,144 A | 6/1999 | Hayashi |
| 5,954,761 A | 9/1999 | Machek et al. |
| 6,010,531 A | 1/2000 | Donlon et al. |
| 6,012,457 A | 1/2000 | Lesh |
| 6,086,582 A | 7/2000 | Altman et al. |
| 6,102,887 A | 8/2000 | Altman |
| 6,159,142 A * | 12/2000 | Alt ..................................... 600/3 |
| 6,161,029 A | 12/2000 | Spreigl et al. |
| 6,164,283 A * | 12/2000 | Lesh ............................ 128/898 |
| 6,179,858 B1 | 1/2001 | Squire et al. |
| 6,206,914 B1 | 3/2001 | Soykan et al. |
| 6,210,392 B1 | 4/2001 | Vigil et al. |
| 6,224,491 B1 | 5/2001 | Hiromi et al. |
| 6,224,626 B1 | 5/2001 | Steinke |
| 6,254,632 B1 | 7/2001 | Wu et al. |
| 6,267,776 B1 | 7/2001 | O'Connell |
| 6,283,992 B1 | 9/2001 | Hankh et al. |
| 6,293,964 B1 | 9/2001 | Yadav |
| 6,296,630 B1 | 10/2001 | Altman et al. |
| 6,305,378 B1 | 10/2001 | Lesh |
| RE37,463 E | 12/2001 | Altman |
| 6,346,099 B1 | 2/2002 | Altman |
| 6,358,247 B1 | 3/2002 | Altman et al. |
| 6,438,427 B1 | 8/2002 | Rexhausen et al. |
| 6,443,949 B2 | 9/2002 | Altman |
| 6,500,186 B2 | 12/2002 | Lafontaine et al. |
| 6,503,247 B2 | 1/2003 | Swartz et al. |
| 6,572,652 B2 | 6/2003 | Shaknovich |
| 6,702,844 B1 | 3/2004 | Lazarus |
| 2001/0044619 A1 | 11/2001 | Altman |
| 2002/0010462 A1 | 1/2002 | Altman |
| 2002/0019623 A1 | 2/2002 | Altman et al. |
| 2002/0026228 A1 | 2/2002 | Schauerte |
| 2002/0026233 A1 | 2/2002 | Shaknovich |
| 2002/0077691 A1 | 6/2002 | Nachtigall |
| 2002/0151918 A1 | 10/2002 | Lafontaine et al. |
| 2003/0069606 A1 | 4/2003 | Girouard et al. |

FOREIGN PATENT DOCUMENTS

| | | |
|---|---|---|
| EP | 0 601 338 A1 | 6/1994 |
| WO | WO 94/07564 A2 | 4/1994 |
| WO | WO 99/55254 A1 | 11/1999 |
| WO | WO 00/36997 A1 | 6/2000 |
| WO | WO 01/19269 A1 | 3/2001 |
| WO | WO 01/26585 A1 | 4/2001 |
| WO | WO 01/26727 A1 | 4/2001 |
| WO | WO 0126585 A1 * | 4/2001 |
| WO | WO 02/00273 A2 | 1/2002 |
| WO | WO 02/24106 A2 | 3/2002 |
| WO | WO 02/071980 A2 | 9/2002 |

OTHER PUBLICATIONS

The Thoracic and Cardiovascular Surgeon, III Supplement, vol. 47, Aug. 1999, pp. 352-356, "*Catheter Ablation of Pulmonary Vein Foci for Atrial Fibrillation*".

The New England Journal of Medicine, vol. 339, Sep. 3, 1998, pp. 659-666, "*Spontaneous Initiation of Atrial Fibrillation by Ectopic Beats Originating in the Pulmonary Veins*".

European Journal of Cardio-Thoracic Surgery, vol. 11, Apr. 4, 1997 (ISSN 1010-7940), pp. 714-721, "*Inhibition of Atrial Fibrillation by Pulmonary Vein Isolation and Auricular Resection—Experimental Study in a Sheep Model*".

Cleveland Clinic Journal of Medicine, vol. 53, No. 1, Jan. 2001 (ISSN 0891-1150), "*Radiofrequency Ablation of the Pulmonary Veins: Can It Stop Atrial Fibrillation At Its Source?*".

Journal of Computer Assisted Tomography, vol. 25, No. 1, Jan./Feb. 2001, pp. 34-35, "*Identification of Pulmonary Vein Stenosis After Radiofrequency Ablation for Atrial Fibrillation Using MRI*".

Pacing and Clinical Electrophysiology, Nov. 2000, vol. 23, No. 11, Part II, pp. 1836-1838, "*Pulmonary Veins-Left Atrial Junction: Anatomic and Histological Study*".

* cited by examiner

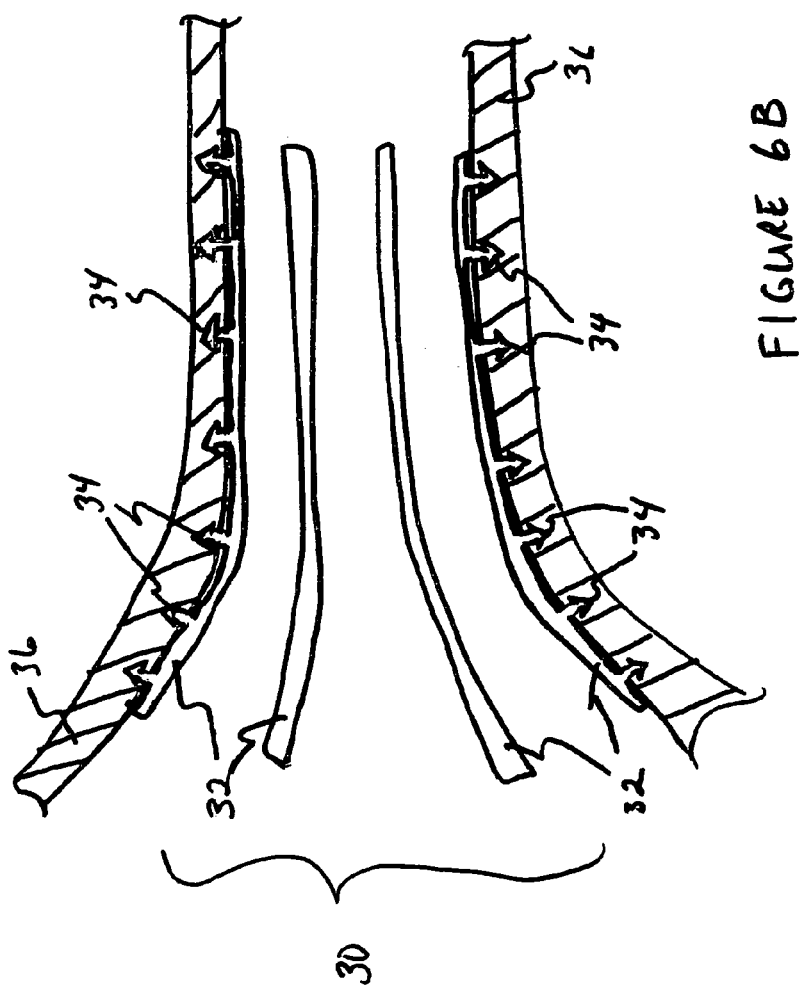

ANTI-ARRHYTHMIA DEVICES AND METHODS OF USE

CROSS REFERENCE TO RELATED APPLICATIONS

The present invention is a continuation of U.S. patent application Ser. No. 10/192,402 filed Jul. 8, 2002, now abandoned which claims benefit of U.S. Provisional Application Ser. No. 60/303,573, filed Jul. 6, 2001; both of which are incorporated herein by reference.

BACKGROUND OF THE INVENTION

Cardiac arrhythmia affects millions of people worldwide and is broadly defined as an abnormal or irregular heartbeat that may involve changes in heart rhythm, producing an uneven heartbeat, or heart rates, causing a very slow or very fast heartbeat. Common types of arrhythmias, explained in further detail below, include bradyarrhythmias and tachyarrhythmias, both being typically ventricular or supraventricular in origin.

Bradyarrhythmias are slow heart rhythms (e.g., less than 60 beats per minute) that may result from a diseased or failing sinoatrial (SA) node, atrioventricular (AV) node, HIS-Purkinje, or bundle branch system, as explained in further detail below. Ventricular arrhythmias are arrhythmias that begin in the lower chambers of the heart. In contrast, supraventricular arrhythmias are arrhythmias that originate above the ventricles of the heart, such as the upper chambers (i.e., atria) or the middle region (e.g., AV node or the beginning of the HIS-Purkinje system). Ventricular and supraventricular arrhythmias are generally characterized by accelerated rates (e.g., more than 100 beats per minute) that exceed what is considered normal heartbeat rhythms (e.g., between 60 and 100 beats per minute).

The most common type of supraventricular arrhythmia is atrial fibrillation, with incidence of more than a quarter-million cases each year in the U.S. alone, and a prevalence of nearly 2.0 per 1000 US patient-years, To better understand the mechanism and characteristics of atrial fibrillation, a general understanding of the mechanical and electrical activity of the heart is helpful. For this purpose, attention is directed to FIG. 1.

FIG. 1 depicts a cross-sectional diagram of a normal, healthy heart 10. The heart 10 is a four-chamber, double-sided pump made of muscle tissue that contracts when subjected to electrical stimulation. The electrical stimulation that produces a heartbeat originates in the SA node 12, located at the junction of the superior vena cava 14 with the right atrium 16, and spreads radially through the atria causing the muscle of the heart's upper chambers to contract and pump blood to the ventricles. From the atria, the electrical signal then converges on the AV node 18, located in the right posterior portion of the interatrial septum. The impulse from the AV node 18 then passes to the bundle of HIS 20, which branches at the top of the interventricular septum 22 and runs subendocardially down either side of the septum, and travels through the bundle branches 24. The signal then passes to the Purkinje system 26 and finally to the ventricular muscle causing the lower chambers of the heart to contract and pump blood to the lungs and the rest of the body After contraction of the lower chambers, the sinus node initiates the next rhythm or heart beat and the entire cycle is repeated. In general, it is rate of discharge from the SA node 12 (also referred to as the normal cardiac pacemaker) that determines the rate at which the heart 10 beats.

This synchrony of contraction between the atria and ventricles produces a normal heartbeat. In its broadest sense, atrial fibrillation (AF) represents a loss of synchrony whereby the atria quiver (beating at a rate of about 600 beats per minute) instead of beating or contracting effectively. The loss of atrial contraction and conduction of electrical signals from the atria to the ventricles often cause blood to pool and clot in the atria, and especially in the atrial appendages. If the clot becomes dislodged from the atrium, it can travel through the bloodstream and create a blockage in a vessel that supplies blood to the brain, resulting in stroke. It is estimated that fifteen percent of all strokes occur in people with AF, which translates to about 90,000 strokes each year in the United States alone.

Conventional therapy or treatment options for AF include medication, AF suppression and surgery Medication or drug therapy is generally the first treatment option employed to control the rate at which the upper and lower chambers of the heart beat. Conventional medications used to treat AF include beta-blockers, such as metoprolol or propanolol, and calcium-channel blockers, such as verapamil or diltiazem, which depress conduction and prolong refractoriness in the AV node. Other medications such as amiodarone, ibutilide, dofetilide, propafenone, flecainide, procainamide, quinidine and sotalol are used to affect the electrophysiology of the heart to maintain normal sinus rhythm and can thereby terminate or, in some cases, prevent AF. Although anticoagulants or blood-thinners such as warfarin or aspirin are not designed to treat AF, these medications are often used to reduce the risk of clot formation and stroke which, as previously discussed, often occur in patient's suffering from AF.

AF suppression, frequently a second treatment option for patients with AF, may be accomplished using an implanted pacemaker to stimulate the heart in a way that preempts any irregular rhythms. In general, the pacemaker stimulates or overdrives the heart at a rate slightly higher than its normal, intrinsic rate. Overdriving the heart enables the device to control the heart rate and, thereby, suppress potential episodes of AF.

Another alternative treatment for AF is surgery. In general, an electrophysiology study is first performed to characterize the arrhythmic event. This study usually includes mapping the exact locations of the electrical impulses and conduction pathways along the cardiac chambers using conventional mapping techniques. After locating the cardiac tissue that is causing the arrhythmia, the tissue is then surgically altered or removed to prevent conduction of aberrant electrical impulses in the heart. One example of a surgical procedure used to treat cardiac arrhythmias is the Maze procedure.

The Maze procedure is an open-heart or percutaneous surgical procedure designed to interrupt the electrical patterns or conduction pathways responsible for cardiac arrhythmia. Originally developed by Dr. James L. Cox, the Maze procedure involves carefully forming a "maze" of surgical incisions (from which the procedure's name is derived) in both atria to prevent the formation and conduction of errant electrical Impulses, while still preserving the function of the atria. The incisions channel or direct the electrical impulses along the heart to maintain synchrony of contraction between the atria and ventricles of the heart, thereby producing a normal heartbeat, in addition, resulting scar tissue generated by the incisions also prevents formation and conduction of aberrant electrical signals that cause AF, thereby eradicating the arrhythmia altogether.

Although surgical intervention, such as the Maze procedure, has proven successful in treating AF, these procedures are highly invasive, generate many post-operative complications, require lengthy patient recovery times and are quite costly. As a result, minimally invasive ablation techniques have become more popular and have been offered as an alternative treatment to surgical intervention for patients suffering from AF.

Cardiac ablation techniques typically involve the removal or destruction of cardiac tissue and the electrical pathways that cause the abnormal heart rhythm. In general, cardiac ablation is less costly, has fewer side effects and requires less recovery time for the patient compared to more invasive procedures. There are various methods by which a cardiac ablation procedure may be performed. These methods and energy modalities include cryoablation, radiofrequency (RF) ablation, laser ablation, microwave, vaporization, balloon ablation, drug elution and photodynamic therapy.

During an ablation procedure, an electrophysiology study is first performed to characterize the arrhythmic event and map the precise locations that exhibit the arrhythmia. Once these sites are identified, an ablation catheter is maneuvered to each of these sites and a sufficient amount of energy is delivered to ablate the tissue. As a result, the energy destroys the targeted tissue and, thus, makes it incapable of producing or conducting arrhythmia, while leaving the adjacent healthy tissue intact and functional.

In addition to ablating the specific arrhythmic tissue sites, alternative ablation procedures, such as cardiac segmentation procedures, have been developed to mechanically isolate or re-direct errant electrical signals in the heart. These procedures typically involve forming one or more linear or curvilinear lesions in the wall tissue of the heart to segment the cardiac chambers, similar to the above-described Maze procedure. These segmented lesions are generally formed in the atrial tissue of the heart, although accessory pathways, such as those through the wall of an adjacent region along the coronary sinus, have also been produced.

Advances in mapping and characterizing cardiac arrhythmias, particularly AF, have provided much insight into the mechanism of AF. Research has shown that there are at least six different locations in the left and right atria of the heart where relatively large, circular waves of continuous electrical activity (i.e., macro reentrant circuits) occur in patients suffering from AF. Recently, it has been determined that these reentrant circuits or wavelets may actually be confined to a limited area near the pulmonary veins. In other words, some forms of AF may even be triggered or maintained by a single focus of automatic firing. As a result, several procedures have been developed whereby one or more ablation segments or lesions are formed in tissue to isolate the pulmonary veins and thereby block the electrical impulses that cause AF.

Although catheter based ablation procedures are less invasive than conventional surgical procedures, there are various complications that may occur. Examples of possible complications include ablation injuries, bleeding, hematoma, pericardial effusion and cardiac tamponade, failure of the procedure, scar formation and stenosis. In addition, the time course of lesion maturation and scar formation following cardiac ablation procedures often result in delayed onset of electrical isolation and high incidence of post-operative atrial fibrillation.

In view of the above, there is a need for a minimally invasive device and more effective and efficient methods to treat cardiac arrhythmias. In particular, it is desirable that the methods have a high success rate at treating arrhythmias, have minimal to no side-effects or related complications, and can be completed more rapidly than conventional methods. In addition, the treatment methods should also reduce patient recovery times and hospital costs. Overall, the method of treatment should also improve the quality of life for patients.

BRIEF SUMMARY OF THE INVENTION

In general, the present invention contemplates an implantable device and method for modifying conduction, electrical connection and propagation properties in a tissue and/or treating cardiac arrhythmias. The device comprises a structural platform made of a biocompatible material, wherein the platform may be conformable to a shape of a target tissue site. In addition, the platform may also include a treatment component sized and shaped to induce a fibrotic response in the target tissue. The treatment component may also be configured to cause sufficient fibrotic response so as to substantially eliminate cardiac arrhythmias.

The present invention also contemplates a method of treating cardiac arrhythmias. In generals the method comprises delivering a treatment device to a target site and manipulating the device to conform a shape of the device to a shape of the target site. The method may also include modifying a tissue makeup at the target site and allowing the modification of tissue makeup to proceed so as to induce a response that results in electrically decoupling the tissue. The method may further include leaving the treatment device implanted at the target site.

Additionally, the present invention contemplates a device for modifying tissue at a target tissue site of an organ, wherein the device comprises at least one deployment platform. The deployment platform may include a treatment component configured to induce a material tissue response at the target tissue site. In addition, the treatment component may also be configured to induce a material tissue response sufficient to modify local physiologic properties of the organ so as to achieve a desired therapeutic goal for the organ.

The present invention also contemplates a method of inducing a material tissue response at a target site, wherein the method includes delivering a treatment device to the target site and ensuring contact of a treatment component of the treatment device with tissue at the target site. The method may also include inducing the material tissue response at the target site as a result of ensuring contact of the treatment component with the tissue and allowing the material tissue response to continue at the target site at least until a therapeutic goal is substantially achieved.

BRIEF DESCRIPTION OF THE DRAWINGS

Other features and advantages of the present invention will be seen as the following description of particular embodiments progresses in conjunction with the drawings, in which:

FIGS. 6A and 6B are sectional views of various embodiments of an implanted device in accordance with the present invention.

DETAILED DESCRIPTION OF THE INVENTION

In one preferred embodiment of the invention, a stent-shaped device 30 may be used to treat, prevent and/or terminate arrhythmias. It should be noted that use of the term "stent" is not meant to be limiting but, rather, is used for reader convenience and brevity. In general, the device 30 resembles an "inverse sock" fabricated from a fine netting material (e.g., Nitinol®, spring-tempered stainless steel, cloth fiber, etc.). The netting material may be self-expandable, causing the device 30 to tightly conform to the structure into which it is placed. In one embodiment, a high spatial frequency of fine material (i.e., fine fibers, elongate elements (discussed in further detail below) or strands) is used to fabricate the device 30. This design provides the device 30 with added axial conformability and trans-axial capabilities, resulting in improved tissue adhesion and fit.

The device or deployment platform 30 of the present invention may also be characterized by its ability to bend longitudinally and trans-axially. This capability enables the device 30 to conform to any desired biologic shape, including, but not limited to, the wall of an artery, vein, cardiac chamber or other biologic target structure. In addition, the device 30 may also be characterized by its ability to expand in a radial direction, and continue to conform to a shape that may change. In one embodiment, the device 30 may have a maximum size, beyond which the device 30 does not expand. This configuration prevents the tissue structure 36, into which the device 30 is placed, from growing or expanding above a predetermined size.

Figure 1:
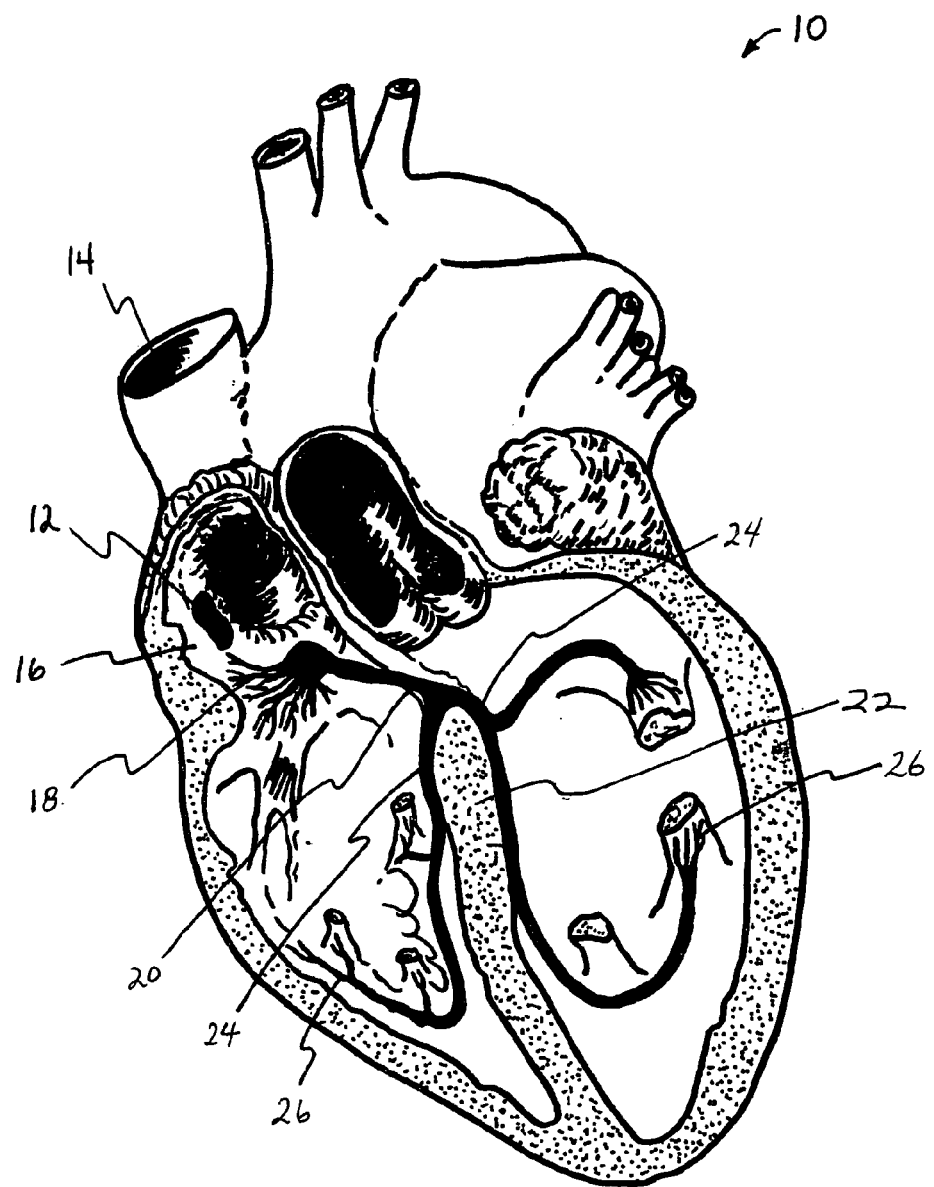
FIG. 1 is a cross-sectional diagram of a normal, healthy heart.
Figure 2A:
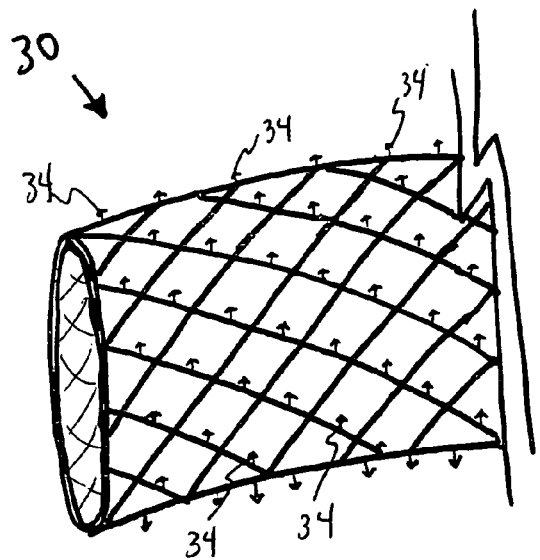
FIG. 2A illustrates another embodiment of the device in accordance with the present invention.
Figure 2B:
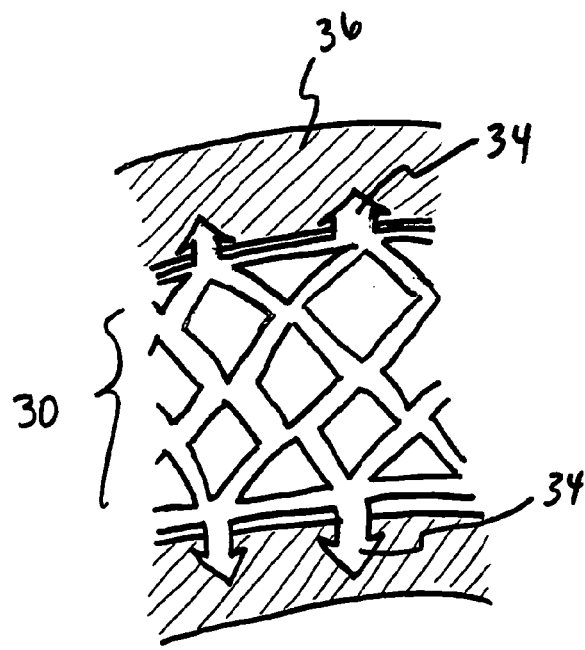
FIGS. 2B and 2C are sectional views of other embodiments of an implanted device in accordance with the present invention.
Figure 2C:
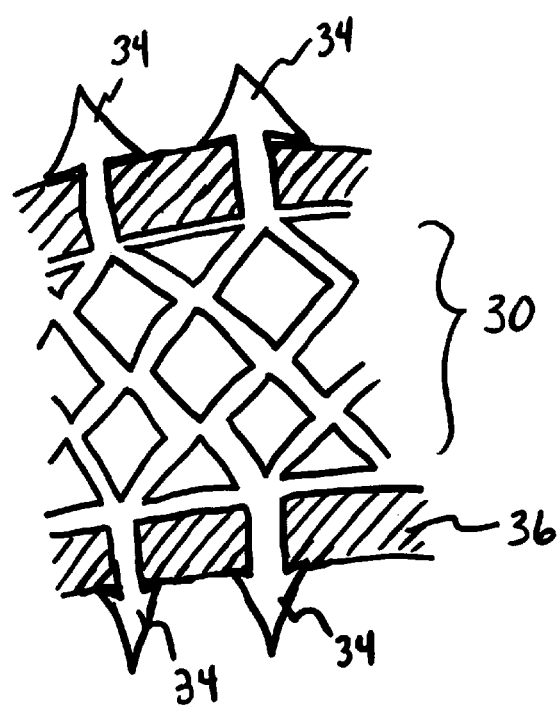

As shown in FIG. 2A, one or more hollow protrusions 34 (discussed in further detail below) lie on an external surface of the device 30. Upon radial expansion of the device 30, via self-expansion, balloon expansion, or other means, the protrusions 34 pierce or embed into the tissue 36 target site of the lumen, as illustrated in FIG. 2B. The protrusions may penetrate the vessel wall either partially or completely (as shown in FIGS. 2B and 2C), gaining access to any cells at any location in or on the structure. The protrusions may also be solid rather than hollow, as may be desirable if drug delivery is not contemplated. In addition to anchoring the device 30, the protrusions also serve various other functions as described in further detail below In one embodiment, injection from a drug delivery balloon (not shown) causes the hollow protrusions 34 to conduct the drug to the adventitial surface of the lumen or vessel. The drug may then cause cell death, fibrosis or inflammation, all of which may be used to combat arrhythmia depending on the type of drug used and desired tissue response.

As disclosed in further detail below, the device 30 of the present invention and its methods of use are designed to achieve a variety of therapeutic goals including, but not limited to, prevention, treatment and/or elimination of arrhythmias. Studies have shown that some forms of AF originate in the pulmonary veins 44 or coronary sinus. More specifically, it has been determined that sources of AF originate in atrial tissue that is on the surface or ingrown into the vessel as it enters the left atrium (i.e., at or near the ostium of the vessel entrance into the atrium). Although further references will be made specific to the pulmonary veins 44, it is understood that other vessels (e.g., coronary sinus, aorta, abdominal aorta, pulmonary artery, atrium, cerebral vessels, etc.) are also included within the scope of the present invention.

When positioned at this target site, the device 30, preferably in an expanded state, eliminates or neutralizes the electrical activity and conductivity of the atrial cells on the pulmonary vein so that AF stimulation is either prevented (by ablating the atrial cells) or the impulses are prevented from propagating into the atrium. In principle, it is distortion of the anatomy, such as the ostium, by a luminal or extra-luminal device 30 that permits sclerosis, cell death, scar formation, mechanical injury, laceration or any combination of these results to attack impulse stimulation and conduction. The following are but a few examples of atrial tissue ablation methods. It is understood that other tissue modification and ablation methods though not specifically disclosed herein are also included within the scope of the claimed invention.

In one embodiment, the device 30 (with or without grasping members, as discussed in further detail below) is radially expanded, for example via self-expansion and/or balloon expansion, in the lumen or outside the lumen (e.g., on the adventitia) of the pulmonary vein 44. Alternatively, the device 30 may be expanded on an endocardial 40 or epicardial 42 surface of the heart. Expanding the device 30 sufficiently beyond the normal diameter of the pulmonary vein 44 causes the vessel to severely stretch, which induces cellular changes that alter the biologic behavior of the tissue 36.

In particular, the fine network of blood vessels called the "vasa vasorum," which are located on the outer surface of many blood vessels and supply the vessel wall itself with blood, are subsequently compressed by this over-stretching, resulting in fibrosis. This vessel over-stretch may further produce tissue/vessel ischemia and other tension effects that may also induce fibrosis The fibrosis may be induced by many mechanisms including, but not limited to, growth factors (Hypoxia Inducible Factor-1 alpha (HIF-1alpha), Vascular Endothelial Growth Factor (VEGF), etc.) and cytokines.

Lack of blood to the atrial cells combined together with the fibrosis induced by the over-stretching renders the atrial cells inactive. However, any unaffected cells upstream from the over-stretched area can still produce the stimulatory potentials. While these cells may still produce a stimulus, it cannot be propagated through the fibrotic area in and/or on the vein due to the fibrosis electrically decoupling the affected cells.

Vessel over-stretch, or other mechanical tissue change, is accomplished initially by deployment of the device 30. However, continued or chronic over-stretch may be achieved by simply maintaining the oversized device 30 within the vessel. As such, the over-stretch itself may also be enough to induce adventitial and/or medial fibrosis simply due to the stretch process.

The purpose of the fibrosis induced by the device 30 may be several-fold. In one embodiment, the fibrosis may serve to mechanically prevent organ or gross body expansion. For example, the structural component of the device 30 may be tailored to expand only to a certain degree. Fibrosis formed in the tissue 36 functions to tightly attach or "glue" the device 30 to the tissue. Moreover, the fibrosis serves to anchor the tissue of interest to the supporting structure/device 30, and even integrate the device completely into the tissue. As such, further expansion of the biological structure is prevented due to the mechanical properties of the device 30 and due to the fibrosis itself (which may develop and grow to contain collagen that will further inhibit mechanical expansion).

Alternatively, the fibrotic response from the expandable device 30 may enable the tissue 36 to retain sufficient pliability to maintain normal tissue (or body organ) function, yet increase its overall structural strength. For example, fibrosis may be induced to strengthen the wall of a cardiac ventricle when the device 30 is placed on the inside of the chamber/structure, while still allowing the ventricle to contract, move and fulfill its normal function. However, the fibrosis also prevents ventricular expansion beyond a certain predetermined size. In general, the material makeup of this type of pliable fibrous tissue comprises more elastin and other pliable materials than collagen.

Alternatively, the fibrotic response may be stimulated to a severe degree causing a process of negative remodeling or contraction. This response, well known by those skilled in the art, results in natural scar formation that promotes wound contraction or shrinkage. The amount of fibrosis contraction may be controllable, via device materials, structure and other components, and may range from no remodeling to a small/medium/large amount of negative remodeling (resulting in contraction) This would be of particular use in preventing expansion of an aneurysm, as in the abdominal aorta or the cerebral vessels. The degree of remodeling is based upon the pre-selected application and desired response.

In addition to device expansion, device materials and structure may also be used to biologically guide the cellular and biologic features of the eventual tissue response and/or therapeutic goal. For example, the device 30 may be configured to induce elastance in the tissue or an elastin-rich fibrosis (e.g., stimulate elastin synthesis and cellular growth) that is quite flexible and visco-elastic. Alternatively, the device may be configured to stimulate growth of densely packed collagen that may mimic the need for such bioabsorbable tissue 36. In the case of collagen, the induced tissue 36 is quite inelastic and, thus, prevents tissue and device expansion. As such, inducing a simultaneous combination of elastin and collagen may simulate any range of mechanical properties for both tissue 36 and device 30.

In an alternate embodiment the device 30 may be configured to control the biologic features of the fibrosis and its cellularity. For example, a highly cellular scar may be formed or, alternatively, less cellular tissue may be produced due to device structure and/or materials. In another embodiment of the invention, the device 30 may be coated with a material to stimulate less collagen or elastin growth and increased glycose-amino-glycan and other components of extra cellular matrix production.

There are numerous additional methods by which to induce fibrosis, thereby preventing aberrant impulse conduction through tissue 36. In addition to over-stretch injury, inflammation and toxicity may also be used, as discussed further below.

Inflammation induced fibrosis may be accomplished using an embodiment of the device 30 having prongs or tissue grabbers 34 that penetrate partially into or completely through the vessel. A chemical irritant located on the surface of the prongs 34 causes the desired inflammation and, thereby, induces fibrosis in the atrial tissue 36. In general, the fibrosis occurs in and around the three-dimensional structure and, thus, it is the structural configuration of the device 30 that guides/determines the eventual fibrosis configuration. As discussed in further detail below, the device 30 may be configured in any arbitrary shape, size and density and may include one or more of a variety of chemicals/agents/substances. Alternatively, the device 30 may be placed only against the interior surface and tissue ablation may still occur on the outer surface of the biologic structure.

In an alternate embodiment, only the tips of the prongs 34 are coated with a chemical irritant, the remainder of the stalk of each prong 34 being uncoated and, thus, inactive. Further, the interior of the prongs 34 may house additional chemical irritant that elutes out into the outer regions of the vein, thereby gradually inducing a fibrotic response that prevents initiation or propagation of the arrhythmia. Examples of such chemical irritants include, but are not limited to, metallic copper, zinc, talc, polymers, drug-eluting polymers, tetracycline or other fibrosis-inducing substances.

In another embodiment of the invention, a toxic substance may also be used to induce fibrosis. The substance is released into the tissue 36 by the device 30, via a delivery device and/or any of the previously disclosed methods, and either kills atrial cells or prevents their depolarization and/or conduction. Thus, the resulting fibrosis or scarring inhibits cell stimulation and/or impulse propagation and, thereby, prevents or terminates the arrhythmia. Examples of toxic substances include, but are not limited to, metallic copper, zinc, polymers, poly-lactic acid, poly-glycolic acid, tetracycline, talc or any other chemicals/agents/substances capable of fibrosis induction.

Use of a conventional stent-shaped device 30 near the atrial entrance of the pulmonary vein 44, or entrance of any other vessel, generally distorts the ostium-atrial entrance geometry in a radial (i.e., outward, trans-axial) direction. As previously discussed, this configuration may be effective in attacking arrhythmias since cell/tissue death or fibrosis may successfully interrupt the conduction/stimulation of AF. In some instances, there may be cells extending up and down the ostial wall that may escape the fibrotic process. In such an instance, a flared device may be used.

Figure 3A:
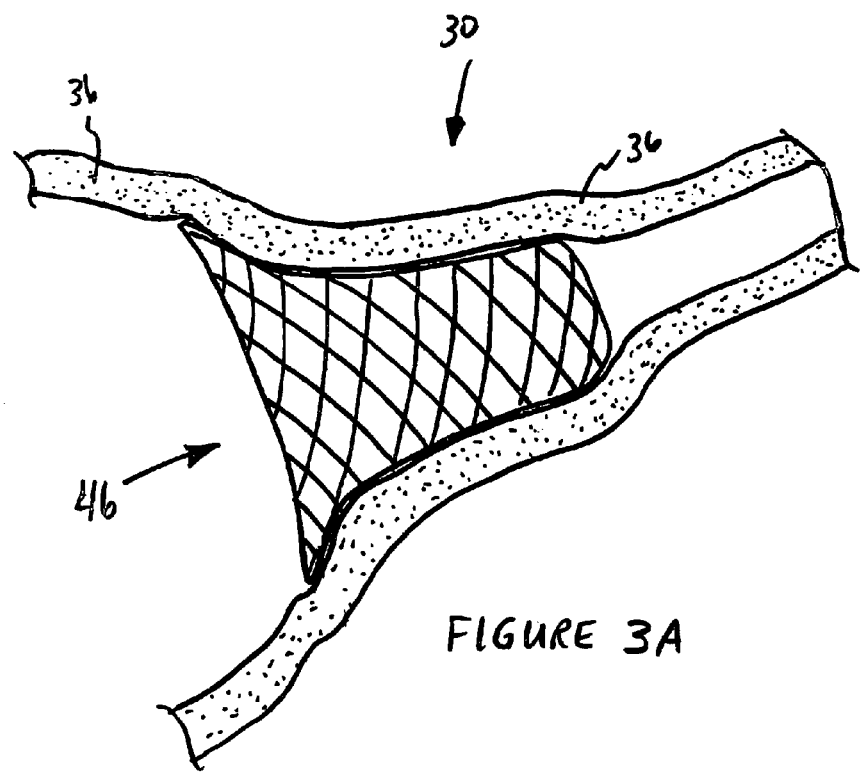
FIGS. 3A-3C illustrate sectional views of various embodiments of an implanted device in accordance with the present invention.
Figure 3B:
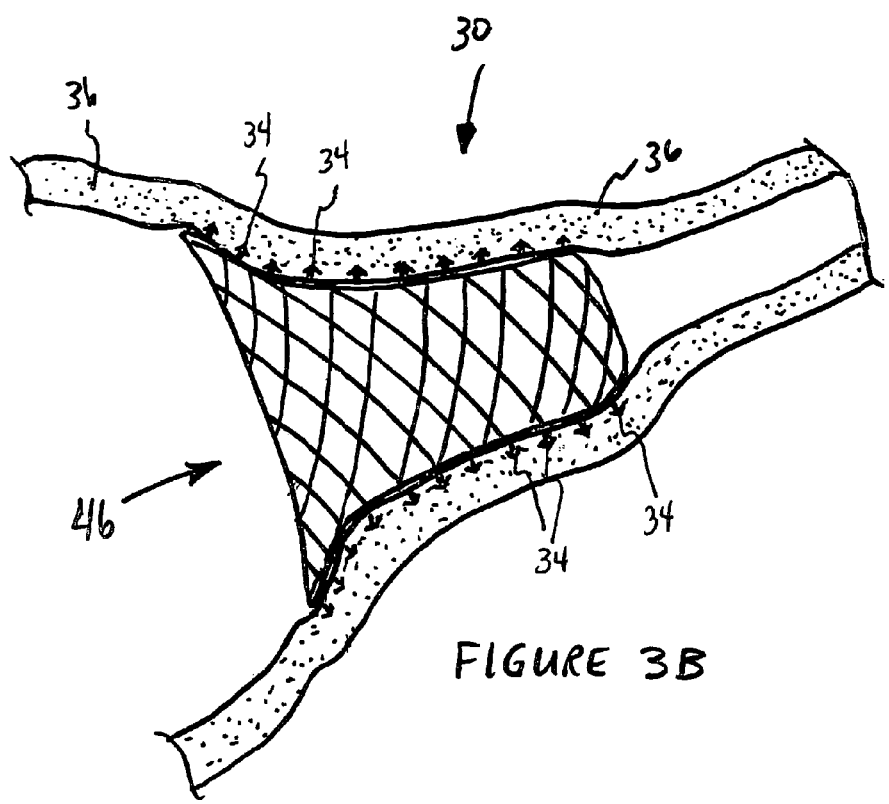

Referring to FIGS. 3A and 3B, an alternate embodiment of the device 30 of the present invention includes one or more outwardly flared portions 46 When positioned within a patient, the flared end 46 is located at or near the ostium or vein-atrial interface. In addition to anchoring the device 30, this device configuration also draws tissue into the ostium and, in so doing, causes the cells to cease conduction, either by death or fibrosis. Inevitably, distortion of the ostium prevents propagation or conduction of impulses into the atrial tissue 36 and, thereby, terminates arrhythmias.

This mechanical distortion of the tissue and/or ostium geometry, in effect, brings the ostium into the lumen of the device 30. In other words, cells that were previously within the atrium at the ostial site are relocated within the new lumen created by the mechanical support of the device 30.

Figure 3C:
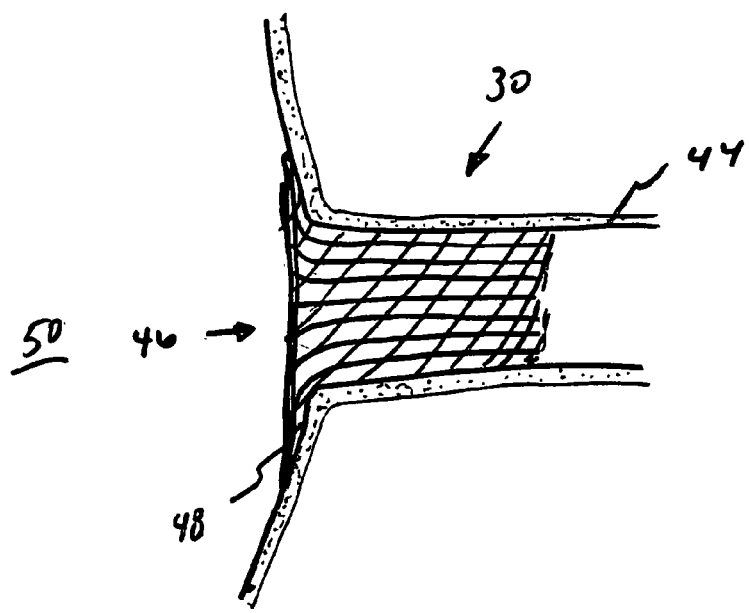

In another embodiment, illustrated in FIG. 3C, the flared end 46 of the device 30 may further include a lip or ring 48 that extends out into the atrium 50. As such, the ring 48 functions to prevent conduction and/or generation of impulses beyond the ostium and, in so doing, terminates AF or prevents its conduction into the atrial tissue.

In general, the device 30 of the present invention functions to stretch not only the vein, but also the ostium. This stretch causes tension in the vessel wall and compression of blood supply in either capillary form or vasa vasorum The resulting compression may further produce tissue ischemia and other tension effects and induce fibrosis and/or collagen/matrix formation to interrupt electrical impulse generation and conduction. As disclosed in further detail below, toxic or inflammatory agents may also be included with the device of the present invention to prevent, treat and/or terminate arrhythmias.

Although compression forces alone may induce an inflammatory response, the anatomy of a device-tethered vein in communication with a free atrial wall and the relative motion between the two structures may also induce irritability and inflammation. Alternatively, the device 30 may also prevent or change this relative motion. However, even in these instances, impulse induction and conduction may still be interrupted or eliminated.

In addition to inducing fibrosis via tissue compression tissue injury or chemical/agent inducement, the device 30 of the present invention may also be used to stimulate proliferation of cells in the adventitial or outside region of a vein or artery, where electrically active cells reside and/or conduction occurs. An illustration of the various tissue layers of an artery/vein is shown in FIG. 4. In general, the vessel 52 includes three layers or "tunics." The tunica intima 54 comprises an inner endothelial cell layer 56 (i.e., the endothelium), a subendothelial connective tissue 58 and a layer of elastic tissue 60 (i.e., the elastica interna). In contrast, the tunica media 62 comprises smooth muscle and the tunica adventitia 64 comprises connective tissue.

Cell proliferation, stimulated by the device 30 and/or methods of the present invention, consists of fibrous tissue, fibroblasts, myofibroblasts and other extra-cellular matrix elements that serve to isolate the electrically active cells that cause the arrhythmia. As such, cells are not necessarily killed or injured, as with ablation techniques. Moreover, the proliferation and stimulation of fibrosis (including fibroblasts, fibrocytes, collagen and extra cellular matrix formation) occurs throughout the vessel wall (i.e., a transmural effect), including within the intima 54.

Cell proliferation and other transmural effects occur from stretch and tension induced in the wall of the artery or vein. The tension within the vessel wall, assuming the wall is relatively thin, is governed by LaPlace's Law: $T=P \times R$ (wherein: T=wall tension, P=pressure within the structure, and R=radius of the structure).

As previously disclosed, tension can cause collapse of arterial or venous vasa vasorum, thereby making the vessel ischemic. Also, if the tension is too high, injury or laceration (small to large, depending on the tension applied) to the vessel may occur. However, it has been shown that such tension may also actually stimulate proliferation of fibrous tissue. Therefore, by controlling the amount of tension or injury (with or without tissue laceration), the degree of fibrosis and proliferation can also be controlled. Moreover, the tissue proliferation is typically proportional to the tension and injury created.

Unlike conventional ablation technologies which promote widespread cell death and cause the intima 54 to thicken to the point where vascular stenosis occurs (an additional complication of ablation procedures), the device 30 of the present invention carefully controls the injury and, thus, does not stimulate such stenosis. For example, the transmural effects of the device 30 and associated methods may affect the adventitia with fibrosis; however, the inner lumen remains relatively unaffected. Moreover, the mechanical and/or structural support offered by the implant 30 further limits or eliminates the problem of fibrosis restricting the lumen (which generally also induces stenosis).

Figure 4A:
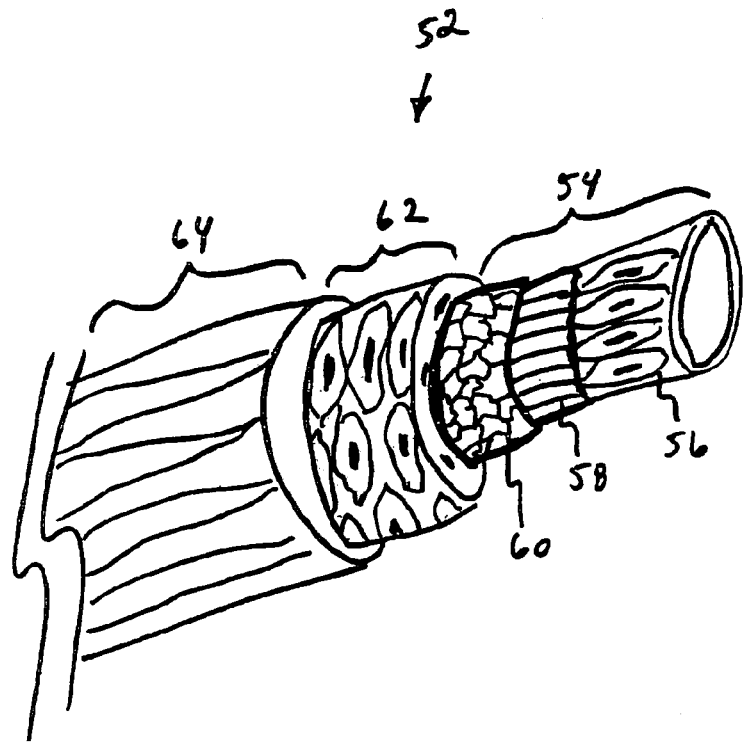
FIG. 4A illustrates the various layers of a vessel.
Figure 4B:
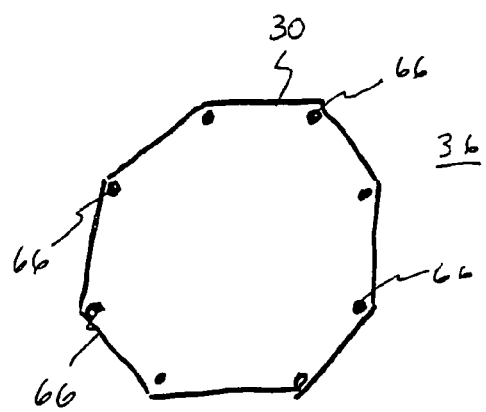
FIG. 4B illustrates areas of high sheer at various tissue points in accordance with the present invention.

For example, high shear at sharp points (such as those shown by reference numeral 66) can be placed at various points on the tissue 36 using the device 30, as shown in FIG. 4A, thus creating localized fibrosis that extends transmurally from intima 54 to adventitia 64. These focal areas can then be used to create conduction isolation/blocks, due to the non-arrhythmic/non-conductive nature of the fibrous tissue and matrix. Thus, it is the fibrotic tissue that prevents conduction or generation of arrhythmic impulses.

Alternatively, the device 30 can also be used to induce fibrosis by inflammation induction. It has been determined that subsequent healing of the inflammation is a long-term cause of fibrosis. This inflammation can be purely mechanical (e.g., stress; tension) or chemical (e.g., copper and/or zinc coating; inflammatory agent coating). As disclosed in further detail below, a chemical agent could also be delivered to the target site by a local delivery mechanism (such as a local drug delivery balloon) prior to or following device delivery. The body's response to the inflammation is to attack the inflammation, thereby producing excess interstitial fibrous tissue which prevents conduction or generation of irregular signals.

In addition to inducing fibrosis, the present invention may also be used to induce calcification of the adventitial region within a vessel, such as the pulmonary vein 44. The calcification process functions to harden soft tissue which interrupts electrical conduction of atrial impulses and, thus, prevents AF impulses from spreading to the atrium. Further, calcification of the coronary sinus can also be performed, in the event that the coronary sinus is involved in the arrhythmic circuit. In general, calcification may be induced in practically any tissue region exhibiting arrhythmia.

One method of inducing calcification is to take blood directly from a patient and inject it into the vascular wall. Alternatively, the blood may be concentrated, for example, by methods of centrifugation or sedimentation by gravity. Since the red blood cells are the apparent inducers of calcification, the blood is first concentrated to separate out these red blood cells. Next, a sufficient amount of red blood cells are then injected directly into the wall of the vessel, Consequently, the tissue 36 becomes relatively hardened or inflexible due to calcification, thereby suppressing or terminating irregular rhythm conduction.

The above-discussed injection may be accomplished using a local drug delivery catheter such as the Infiltrator (manufactured by Boston-Scientific Corp.). The Infiltrator has small needles capable of delivering injectate through the needles and into the wall Of the vessel However, care should be taken so that the needle does not dissect the vessel wail during the injection process. As such, small dissections may be more beneficial and induce a higher calcific volume compared to larger dissections.

In an alternate embodiment of the invention, the device 30 may also be used to prevent or slow growth/expansion of aneurysms. In general, the device 30 creates fibrosis and collagen deposition and promotes cellularity of the aneurysms to hemodynamically stabilize them, thereby preventing growth and rupture. This is accomplished by initially generating a temporary inflammatory reaction that heals with a fibrotic layer. The resulting fibrosis contains cellularity, a feature that sustains the fibrosis, attaches the device 30 to the artery wall, and provides for tong-term stabilization of the biologic-technologic hybrid combination.

This embodiment of the device 30 comprises a percutaneous implant that expands, either through a self-expanding mechanism (similar to those described previously and in further detail below) or via a balloon-expanding mechanism. The device 30 may further exhibit excellent longitudinal and trans-axial flexibility, enabling it to optimally conform to the vessel wall. As such, the device 30 provides a supporting structure that effectively presses the device 30 against the wall of the aneurysm, preventing both expansion and rupture of the aneurysm. The fibrosis serves to irreversibly attach the device to the vessel wall.

In general, a variety of device configurations may be used to treat, prevent and terminate aneurysms. For example the device 30 may be coated with a chemical (similar to those described previously and in further detail below) that induces an inflammatory response. In addition, the device 30 may also include a large structural component combined with a fine netting or mesh. This configuration may provide improved coverage of the internal surface of the aneurysm. As such, when the inflammatory material is pressed against or contacts the intima of the vessel, this induces a subsequent inflammatory response. Additionally, the material may be made to expand only to a certain point, and then become quite stiff/rigid, thereby limiting further expansion of the device 30 and/or aneurysm.

In an alternate embodiment, the material structure or configuration of the device 30 alone may be sufficient to stimulate a thickened response (e.g., cellularity) or create tension that makes the adventitia ischemic, These mechanisms may be similar to those by which a stent induces fibrosis and neointimal thickening in a vessel. Thus, in some instances, the device 30 simply needs to be pressed against the wall of the vessel to induce the desired fibrotic response. Alternatively, it may be the intimal placement of the mesh/inflammatory coating of the device 30 that generates the desired adventitial inflammatory response.

The above-described device 30 (and additional embodiments further disclosed below) may be used to treat a variety of aneurysms, such as abdominal aortic aneurysms, cerebral aneurysms and all peripheral aneurysms of arterial or venous structures. For example, the device 30 may be positioned in the abdominal aorta of a patient with a small to moderate sized aneurysm. This device 30 may also be configured to prevent radial expansion both by mechanical features of the strut and also by the fibrous structure of the induced tissue response. As a result, the device 30 fibroses the aortic wall, gives it a cellular nature, thickens the wall, increases the structural integrity of the organ/abdominal aorta at the aneurysm site, attaches to the wall and/or prevents expansion. The aneurysm is thus "frozen" in size and cannot continue to grow (i.e., limited device expansion also limits aneurysm expansion). This result eliminates the need for future surgical repair and, further, is prophylactic for aneurysm growth.

Similar to the above-described abdominal aneurysm, cerebral aneurysms may also be treated using the device 30 of the present invention. The device 30, generally smaller in size, strengthens the structural integrity of the organ at the aneurysm site and, thus, prevents both expansion and rupture due to the resulting thickened wall structure (i.e., cellularity).

The device 30 of the present invention may be used in a variety of additional applications. In one embodiment, the device 30 may be placed in a vein graft (e.g., saphenous vein graft) that is beginning to degenerate. The device 30 functions to "recline" the vein graft with a layer of device material and/or tissue 36. In general, the density of material determines the amount of cellularity and neointima produced.

In an alternate embodiment, the device 30 may be placed in a vein to "shrink" the venous size, thereby restoring venous valve patency. In yet another embodiment, the device 30 is positioned to encircle the entire atrium, thus providing full internal support as the fibrous tissue develops and restoring/maintaining normal atrial contraction, In another embodiment, the device 30 may be positioned internally of the head as one or More atrial rings. Fibrous tissue growth induced by the device 30 may not only prevent undesired atrial expansion but, further, may terminate AF. In an alternate embodiment, the internally implanted device 30 promotes formation of an endocardial encircling ring that prevents ventricular infarct expansion and, in some instances, ventricular remodeling.

In another embodiment, the device 30 of the present invention may be an elastic band, passive (i.e., requires no energy) and percutaneously implantable device 30 that functions as an arterial shock absorber when implanted at a target site. For example, when placed in an artery or other structure, the device 30 modifies the elasticity of that structure (i.e., the pressure-volume relationship of the structure in a fixed manner that may be linear, or any other simple mathematical function).

To better understand the mechanisms and functional characteristics of this embodiment of the device 30, a general review of blood flow and blood pressure and their affects on vessels/organs is helpful.

In general, blood pressure and flow are in phase (i.e., the phase angle between them is zero) when pulsatile flow is instituted in a purely resistive structure. However, blood flow within the human vasculature is further complicated by curves, bifurcations and vessel compliance. As such, the normal human aorta and large capacitance vessels are not purely resistive structures. The pressure-flow relationship in these organs is partially capacitive, since the walls of these organs expand and contract with the pumping of blood. As a result, pressure and flow differ in phase and, in particular, flow typically leads pressure for pulsatile waveforms, such as those induced by a bolus of blood ejected by the heart into the aorta with each cardiac cycle.

As the human vessel ages it becomes significantly stiffer, resulting in a more purely resistive (less compliant) structure. This means that the blood pressure rises simply because of the arterial stiffness. The heart must expend more work on each heartbeat to pump the blood throughout the body at the higher pressure. Arterial stiffness is a major cause of high blood pressure and, in the long turn, heart failure if the hypertension is not treated. Literally millions of people are under treatment (typically with medication) for hypertension and heart failure.

The device 30 of the present invention, when elastic and placed in the aorta or great vessels, restores elasticity (as previously described and discussed in further detail below) to aging cardiovascular systems that have become stiff, rigid, and cause hypertension. If the applied pressure-volume relationship of the implantable device 30 is appropriately nonlinear, the device becomes a "blood pressure regulator." As such, the device 30 allows any blood pressure up to a pre-defined limit, but prevents higher blood pressures than that limit by expanding to accommodate the volume of ejected blood and prevent pressure rises. By restoring a capacitive vector to the central circulation, the device 30 actually lowers blood pressure without pharmacology.

In general, the device 30 functions as a passive, hydraulic system that absorbs volume in proportion to pressure and has a rapid frequency response. In one embodiment, the device 30 is configured as a scaffold (with, for example, a stent-like configuration) that grows into the artery and becomes part of the vessel. In effect, the device 30 functions as an "arterial shock absorber" after implant. The following are several examples of various embodiments of the device 30 used to treat hypertension.

Figure 5A:
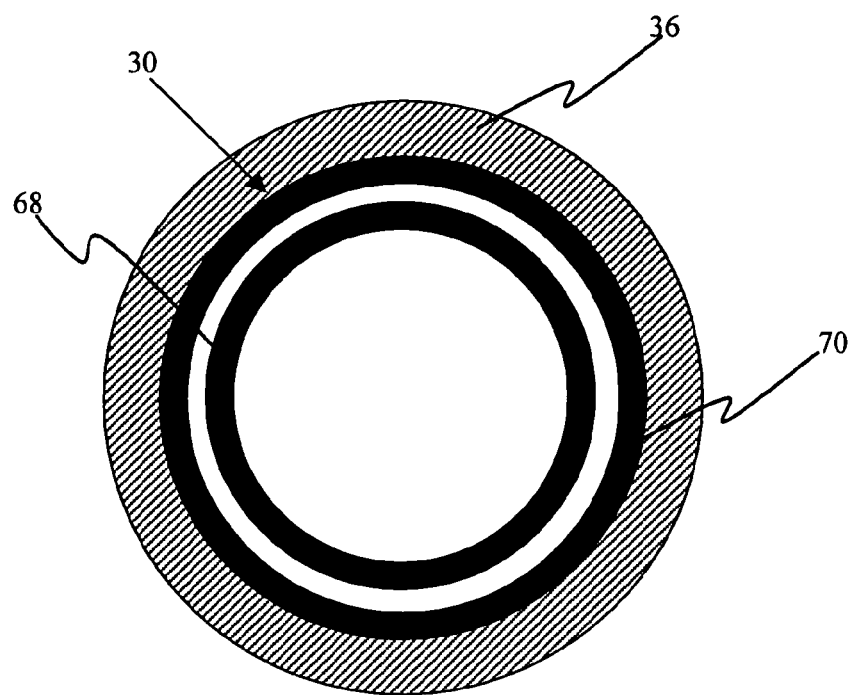
FIGS. 5A and 5B illustrate other embodiments of the device in accordance with the present invention.

In one embodiment, shown in FIG. 5A, the stent-like device 30 includes two concentric, tubular-shaped members 68, 70 that function as a shock-absorber to blood flow/pressure. For example, as a bolus of blood is pumped out of the heart and into the target site where the device 30 is positioned, the inner member 68 of the device 30 compresses against the outer member 70, thereby absorbing, partially or totally, the volume of ejected blood to maintain normal pressure within the system. Generally, the amount of compression is proportional to the pressure; however, nonlinear compression-pressure relationships may also be desirable (as described above) to generate unique properties, such as blood pressure regulation. In some instances, the volume of fluid/blood absorbed may be up to 20% or more of the stroke volume.

In an alternate embodiment, the device 30 may be a fiber band on a circumferential support structure that stimulates elastin growth. As shown in FIGS. 8C-8E, the device 30 may be partially or completely covered with elastin or an elastin epitope. In this configuration, the device 30, in essence, functions to restore the capacitive vector to the vessel/organ 36. For example, as the heart ejects a bolus of blood into, for example, the aorta, the elastin expands to partially accept the volume, thereby preventing the blood pressure from rising as high as would be the case were the vessel rigid (i.e. without the device 30). In general the amount of expansion is proportional to the pressure.

As discussed in further detail below, the device 30 may be fabricated from a variety of materials and configured into various designs. In one embodiment, the device 30 may be completely elastic, due to its material and/or structural characteristics. Alternatively, the device 30 may be elastic and include pores that promote cellular in growth so that the device 30 becomes a living structure within the body.

By restoring the elastic pressure-volume capacitive relationships, the device 30 is useful as a passive (e.g. non-powered), non-pharmacologic method for treating heart failure. This is true not only because blood pressure is lowered, but also because the energy of the failing heart is more efficiently coupled to the arterial system via the compliant nature of the device 30. Thus, if the device 30 functions with minimal energy loss, then the energy is more efficiently coupled.

Figure 5B:
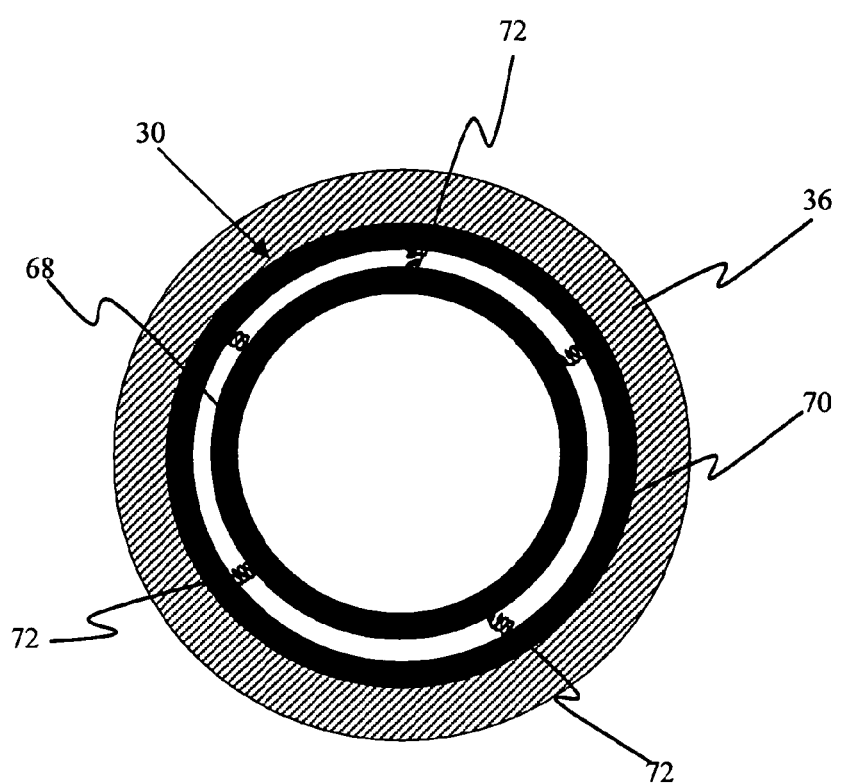

For example, in one embodiment of the invention, illustrated in FIG. 5B, one or more springs 72 (e.g., Nitinol® springs) are located between the two membranes 68, 70 of the device 30. The springs enable the device 30 to function with minimal energy loss such that the resulting system actually conserves energy, an important feature/attribute for cases with failing hearts.

In an alternate embodiment (not shown), the biocompatible device 30 includes inflammation inducing features (e.g., structural chemical, etc.) either on the entire device 30 or on a portion of the device 30. The inflammation may further induce fibrosis which functions to "glue" the device 30 to the inside of an artery or other organ.

In yet another embodiment, the device 30 may also be configured to function as a bladder-like system. This system may include compressibility features that decrease volume with increasing blood pressure.

Although generally passive, the device 30 may include certain features or mechanisms that are externally programmable. Examples of such features/mechanisms include, but are not limited to, variable compliance, variable compressibility, and variable expandability. For example, referring to FIG. 5B, one or more Nitinol® springs of the device 30 may be heated externally in order to change the spring constant. Changing the spring constant may increase (or decrease, depending on the type of change) the amount of device compressibility to that which is more proportional to the hypertension. The ability to transcutaneously heat Nitinol® may yield other programmable features, not disclosed herein but known to those skilled in the art, which are also Included within the scope of the claimed invention.

In another embodiment of the invention, the device 30 may include feedback capabilities. For example, the device 30 of the present invention may measure and transmit pressure readings to another implantable device, such as a biventricular pacing system. This configuration permits literal and real-time feedback to optimize energy transfer and heartbeat within the system.

As previously described, the device 30 is generally a passive, non-powered device. However, these communication or sensing features of the device 30 may require a source of power in order to properly function. In one embodiment, this can be accomplished via the compression/expansion capabilities of the device 30. As the blood pressure causes the device 30 to compress/expand, this energy, in turn, can be captured to generate electrical energy which can then be transferred to power the system. Alternate energy generating systems and means, not disclosed herein but known to those skilled in the art, may also be used and are also included within the scope of the claimed invention.

Figure 6A:
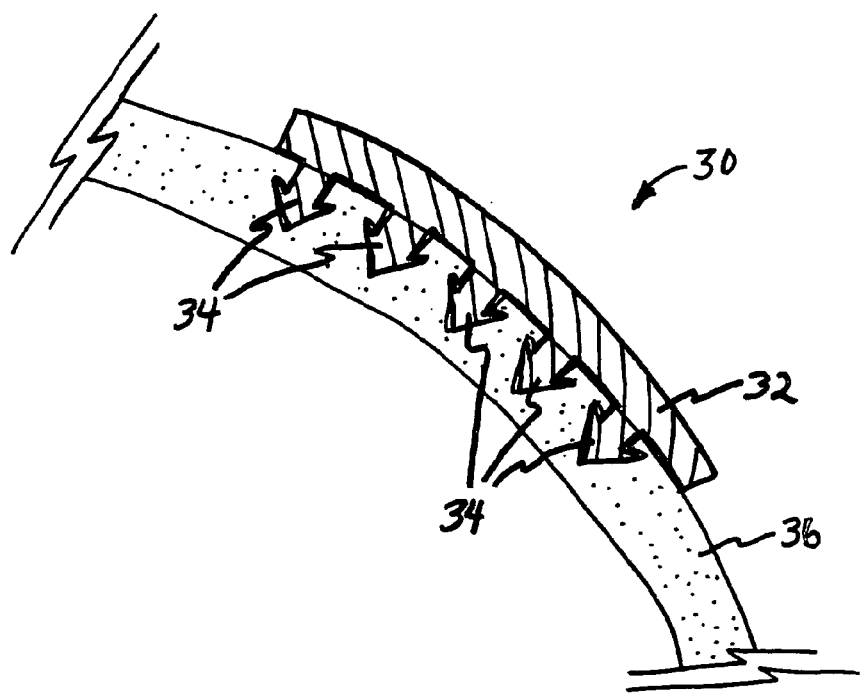
Figure 7:
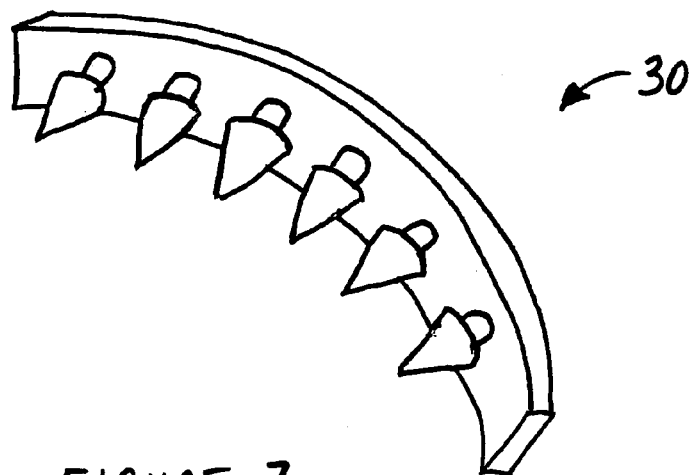
FIG. 7 is a perspective view of an embodiment of the device in accordance with the present invention.

Referring to FIGS. 6A, 6B and 7, an alternate embodiment of the implantable device 30 in accordance with the present invention includes at least one elongate element 32 and one or more protrusions or grasping members 34 that extend into or through tissue 36. In general, the device 30 comprises a sterile biocompatible material and may be percutaneously or surgically implanted on ether an endocardial or epicardial surface of the hear. In an alternate embodiment, the device 30 may be implanted within a lumen of the heart. The size and configuration of the device 30, including the materials from which it is made, are tailored to properly conform to tissue requirements and desired device-induced results. Although the invention as disclosed herein generally refers to the heart, other body organs and cavities, such as pulmonary veins, coronary artery, coronary vein, renal artery, renal vein, aorta, cerebral vessels, coronary sinus or other similar cavities/organs, are also included within the scope of the present invention.

Figure 8A:
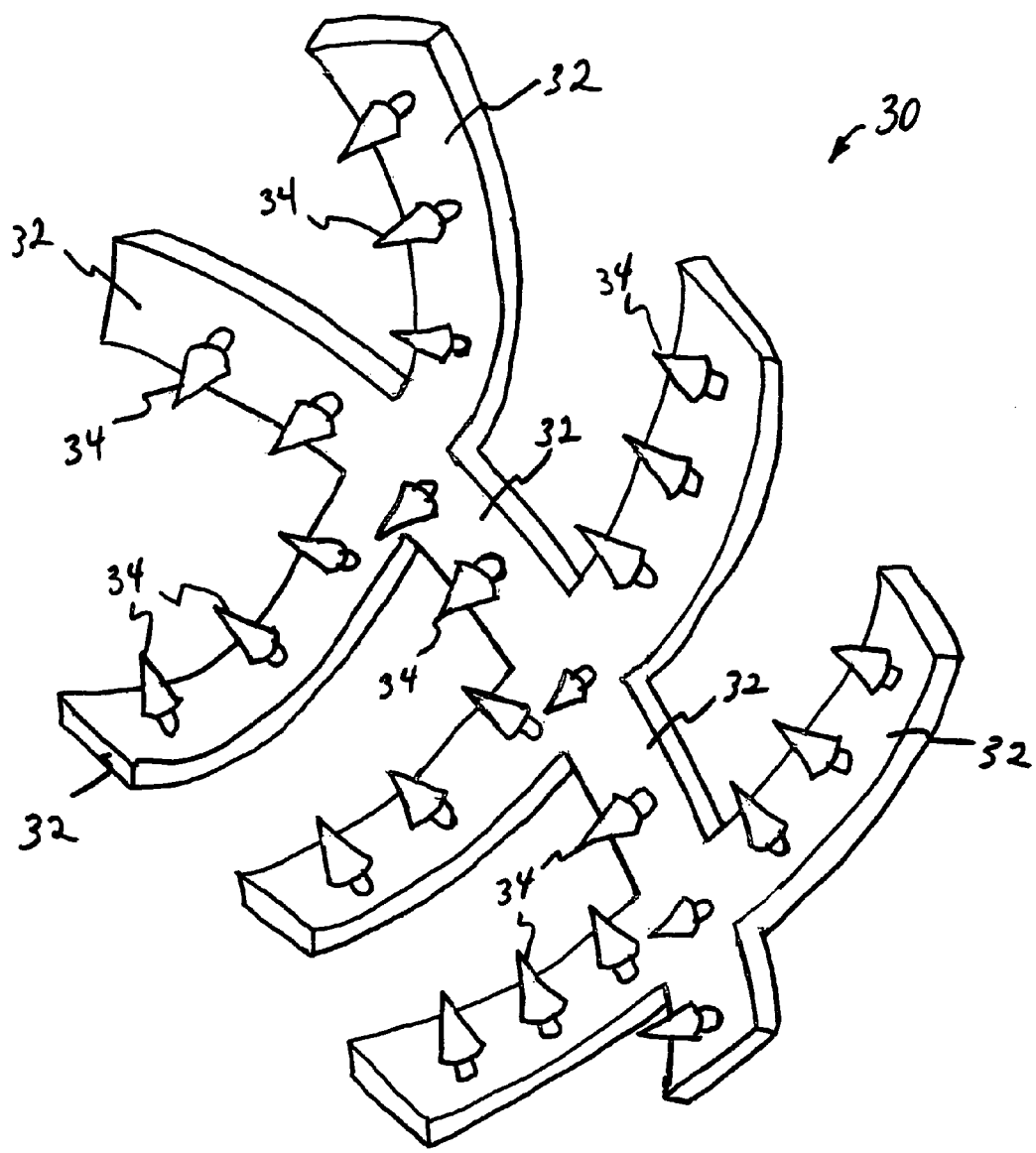
FIGS. 8A-8C illustrate perspective views of other embodiments of the device in accordance with the present invention.

As shown in FIG. 8A, an alternate embodiment of the device 30 of the present invention may include a plurality of elongate elements 32 configured to form a mesh-shaped device 30. This device 30 configuration not only increases the surface area of the device 30 that contacts tissue 36, but may also enhance the structural integrity, flexibility and tissue adhesion characteristics of the device 30.

Figure 8B:
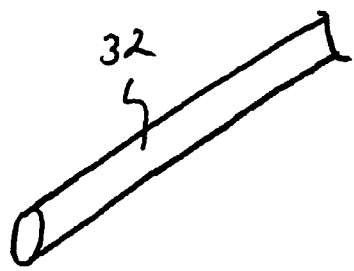
Figure 8C:
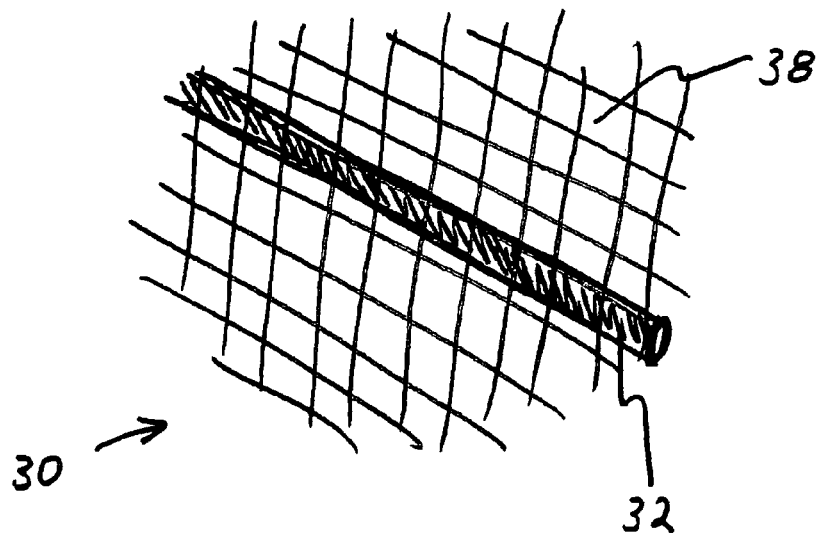
Figure 8D:
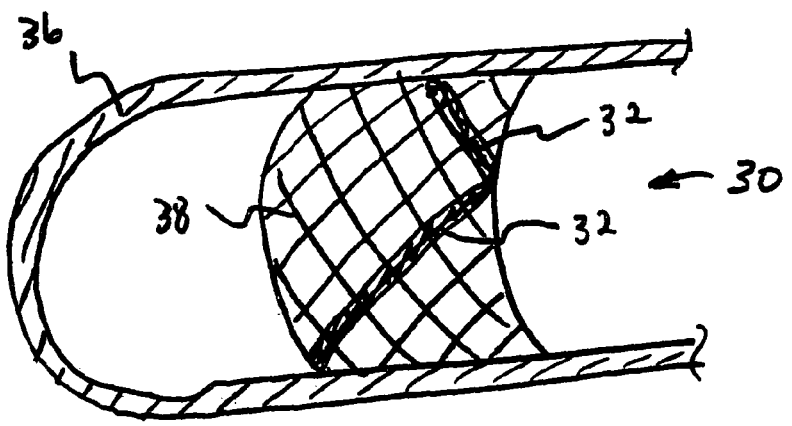
FIGS. 8D and 8E illustrate sectional views of various embodiments of an implanted device in accordance with the present invention.
Figure 8E:
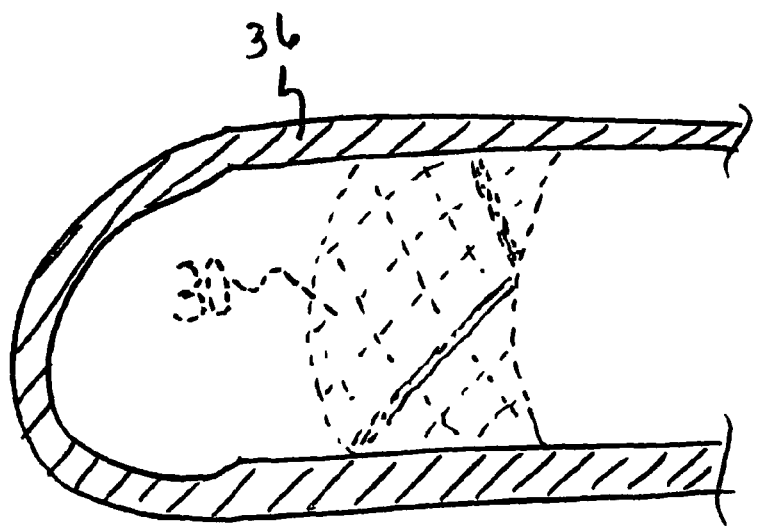

In an alternate embodiment, shown in FIG. 8B, the elongate elements 32 may be rod-shaped to form a type of fiber. The fiber-shaped element 32 may be used alone or in combination with other devices. For example, referring to FIG. 8C, the fiber-shaped element 32 may be combined with a fabric or net 38, thereby functioning as a structural component of the resulting device 30. During use, the device 30 produces the desired fibrotic response through proper tissue contact, shown in FIG. 8D, and/or by becoming integrated within the tissue 36, as shown in FIG. 8E. Additional details concerning device structure and tissue response are described in further detail below.

One or more of the elongate elements 32 or simply portions of the elongate elements 32 may also be configured to an increased thickness/diameter, which may provide increased strength and structural integrity to the overall device 30. Additional device 30 configurations including, but not limited to, ribbon-shaped, spherical, cubical, tubular, rod-shaped, net-shaped, ring-shaped, sheet-shaped and woven, including combinations thereof, are also within the scope of the claimed invention.

The grasping members 34 of the present invention are generally designed to be pushed into and attached to tissue 36, such as muscle, as described in further detail below These grasping members 34 anchor the device 30 to the tissue 36 and, thus, prevent the device 30 from slipping/dislodging or causing embolization within the patient. As such, the grasping members 34 may be configured as darts, studs, barbs, prongs, pointed structures, capped rods and other designs for secure attachment to and/or permanent placement within tissue 36.

A variety of methods may be used to urge the grasping members 34 into the tissue 36. Examples of such methods include, but are not limited to, a radially expanding balloon, a self-expanding device 30 (due to material characteristics of the device 30 or structural characteristics, such as internal struts), an expanding tool, or mechanical force by a physician.

Although the device 30 illustrated in FIGS. 6A-8E includes at least one grasping member 34 designed to penetrate partially or completely through tissue 36, the device 30 may also be configured to include no grasping members 34. Tissue adhesion or attachment may be accomplished via structural or chemical characteristics of the device 30. For example, the device 30 may be configured to conform and, thereby, adhere to an internal or external area of a body cavity. Alternatively, the device 30 may be fabricated from porous materials that promote tissue adhesion and subsequent biological anchoring. Permanent cellular in-growth may further transform the device 30 into a living structure. As such, the living nature of the device 30 permits it to become integrated and thereby last for long periods of time within the body.

Figure 9A:
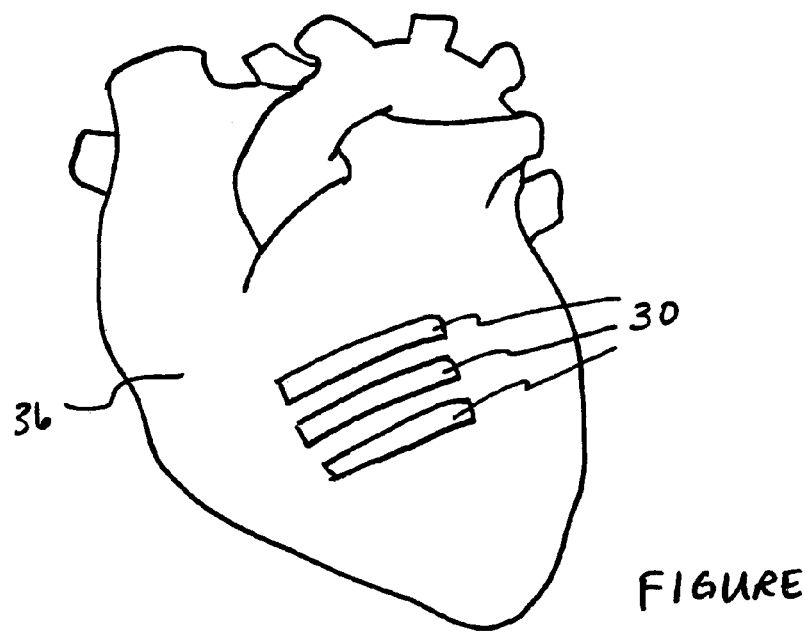
FIGS. 9A and 9B illustrate perspective views of various embodiments of an implanted device in accordance with the present invention.
Figure 9B:
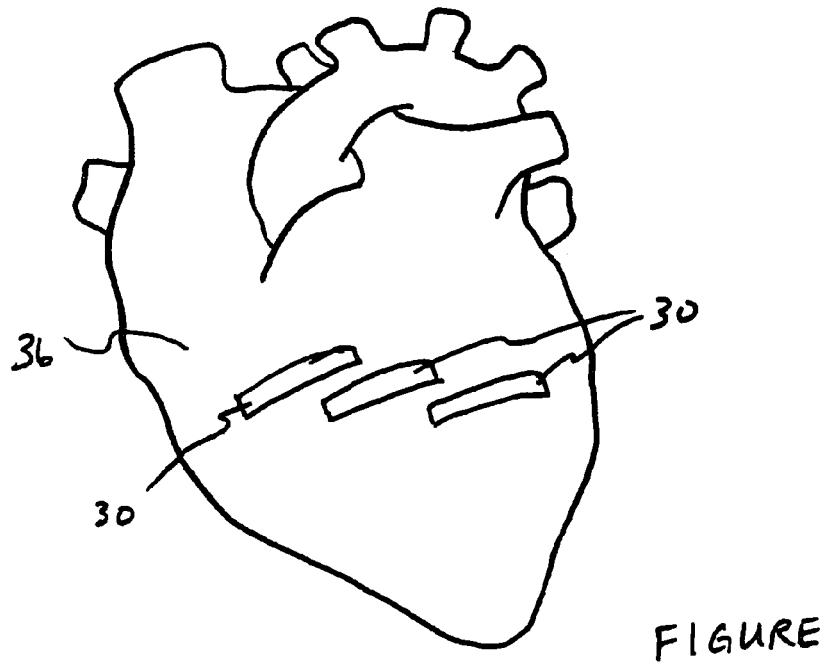
Figure 10A:
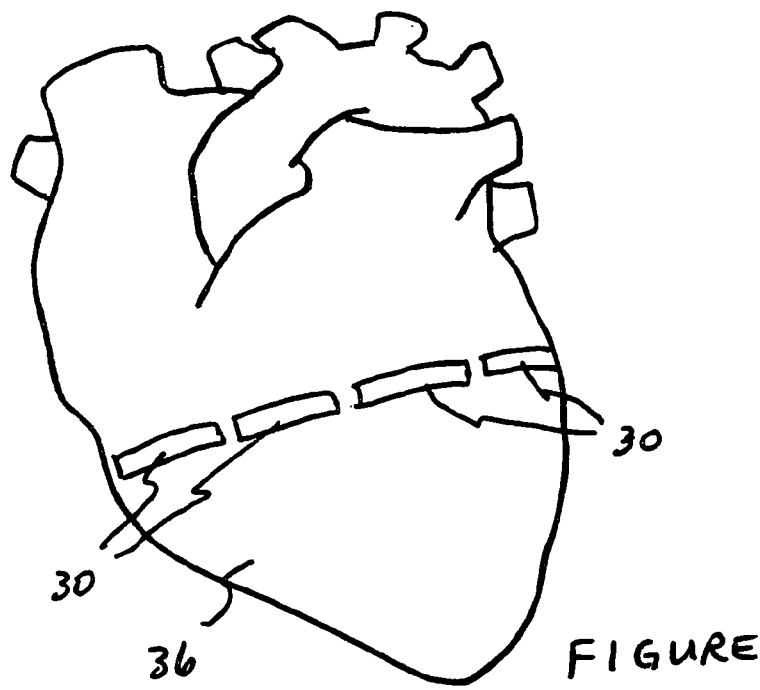
FIGS. 10A and 10B illustrate perspective views of various embodiments of an implanted device in accordance with the present invention.
Figure 10B:
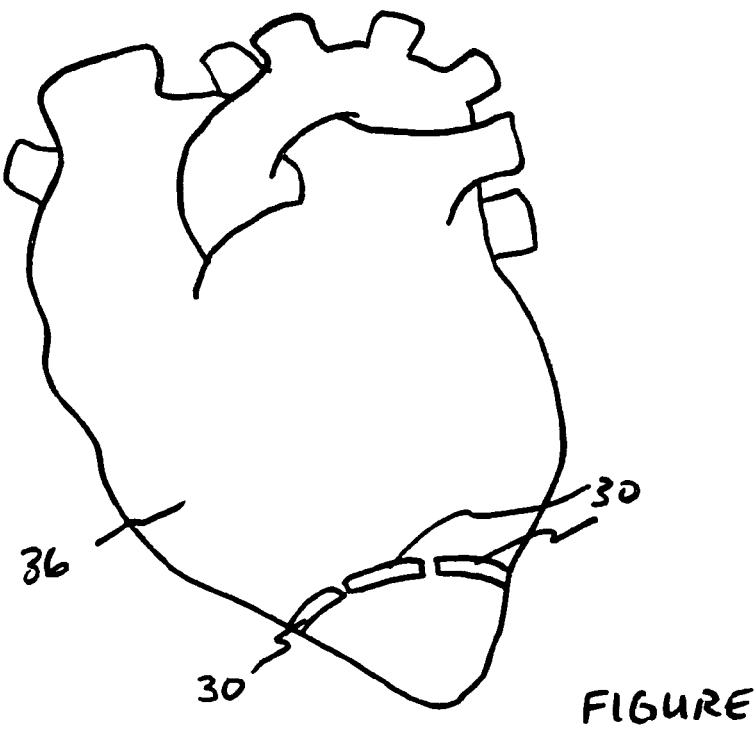

Examples of porous materials used with the device 30 of the present invention include, but are not limited to, ceramics, alumina, silicon, Nitinol®, stainless steel, titanium, porous polymers, such as polypropylene, ePTFE, silicone rubber, polyurethane, polyethylene, acetal, nylon, polyester, and any combination of such materials. Although these materials (and others not specifically described, but included in the scope of the claimed invention) may not be inherently porous, various manufacturing and processing techniques may be used to give the materials the desired porosity characteristics In one embodiment of the invention, the device 30 is made of a conductive material, such as stainless steel. Alternative biocompatible materials including, but not limited to, metals, ceramics, plastics, bioabsorbable materials, bioresorbable materials, biostable materials, absorbable materials, non-absorbable materials or biomaterials, either alone or in various combinations, may also be used In general, the device 30 of the present invention is used to treat, prevent and/or terminate arrhythmias. In one embodiment of the invention, the device 30 is made of a conductive material, such as a metal, and functions as a voltage clamp to short circuit an arrhythmia. During use, the grasping members 34 of the device 30 are pushed into the target cardiac tissue 36. A single device 30 or multiple devices 30 may be placed over a portion or circumferentially around a cardiac chamber, such as the atrium or ventricle, depending on the type and location of the arrhythmia For example, in the case of multiple devices 30, the devices 30 may be placed in parallel (i.e., multiple equatorial bands, shown in FIGS. 9A and 9B) or combined to form equatorial and polar rings, shown in FIGS. 10A and 10B, respectively After the grasping members 34 are inserted into tissue 36, the metallic properties of the device 30, particularly the grasping members 34 which are also made of metal, cause the device 30 to hold the intramyocardial tissue 36 at the same isoelectric potential across the entire device 30. Additionally, when the grasping members 34 of the device 30 extend through the cardiac tissue 36, the isoelectric potential also extends through the entire transmural muscle. As such, since all device-contacted muscle must be isoelectric, the device 30 short-circuits the arrhythmia. Examples of arrhythmias that may be short-circuited by the device 30 include, but are not limited to, atrial fibrillation, reentrant supraventricular tachycardia (SVT), ventricular tachycardia (VT) and Junctional Tachycardia.

Figure 11:
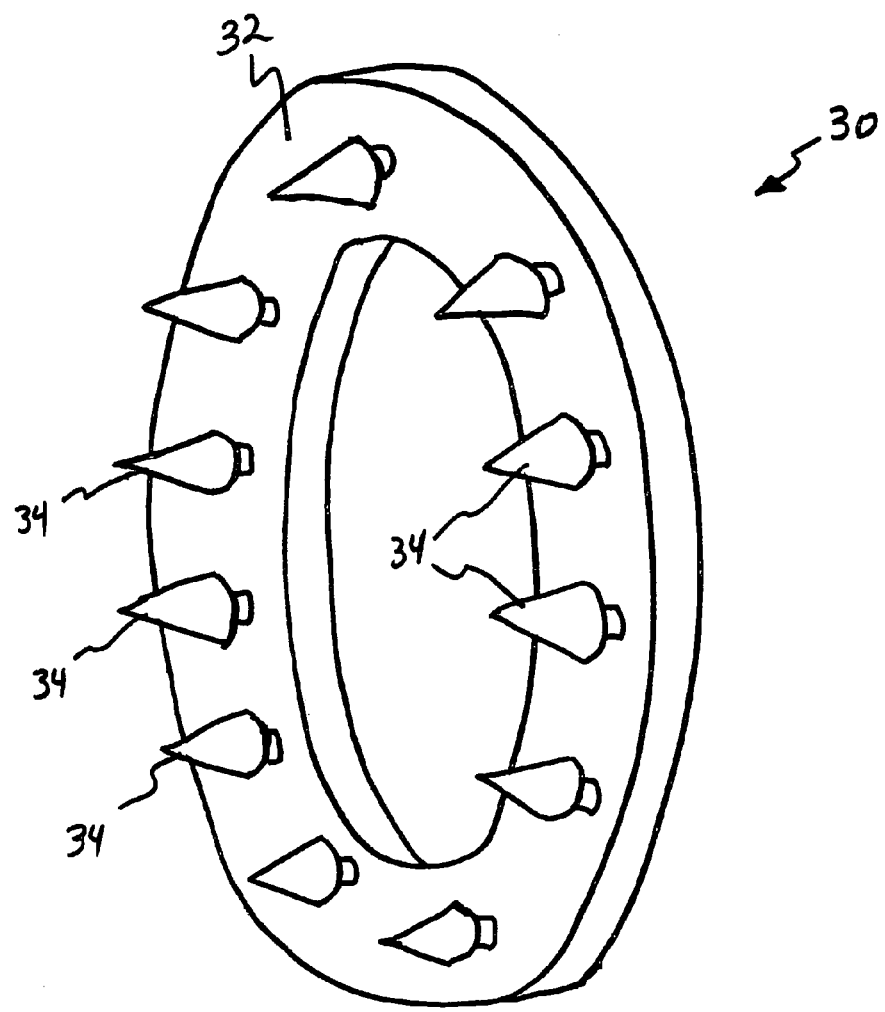
FIG. 11 illustrates a perspective view of a ring-shaped embodiment of the device in accordance with the present invention.

In an alternate embodiment, the device 30 of the present invention may also be used to isolate localized sources of arrhythmias. As previously discussed in the Background of the Invention, some arrhythmias may be triggered or maintained by a single focus of automatic firing. To prevent the aberrant signal from propagating throughout the cardiac muscle, the elongate member 32 is configured into a generally ring-shaped device 30, as illustrated in FIG. 11. However, it is understood that other device configurations optimized to isolate the particular arrhythmia at a specific tissue site may also be used and are hereby included within the scope of the claimed invention.

Figure 12A:
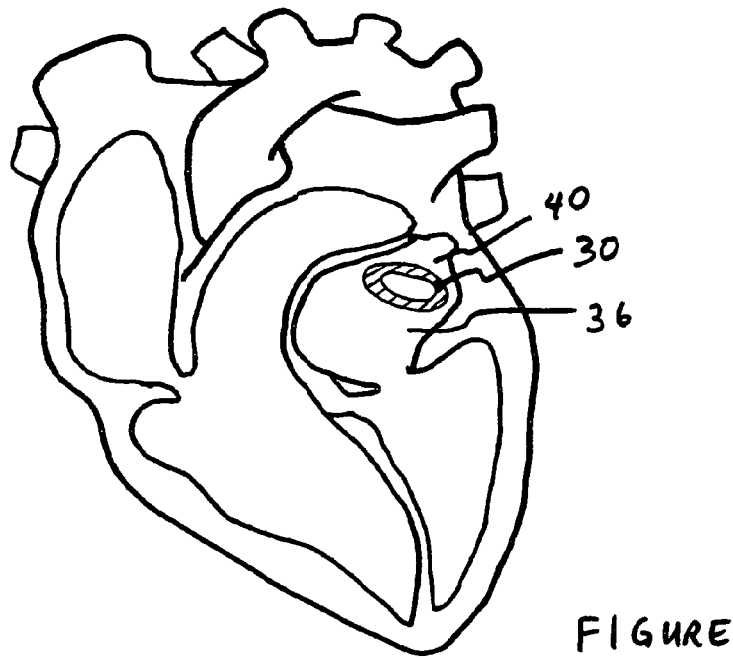
FIGS. 12A-12C illustrate sectional views of various embodiments of an implanted device in accordance with the present invention.
Figure 12D:
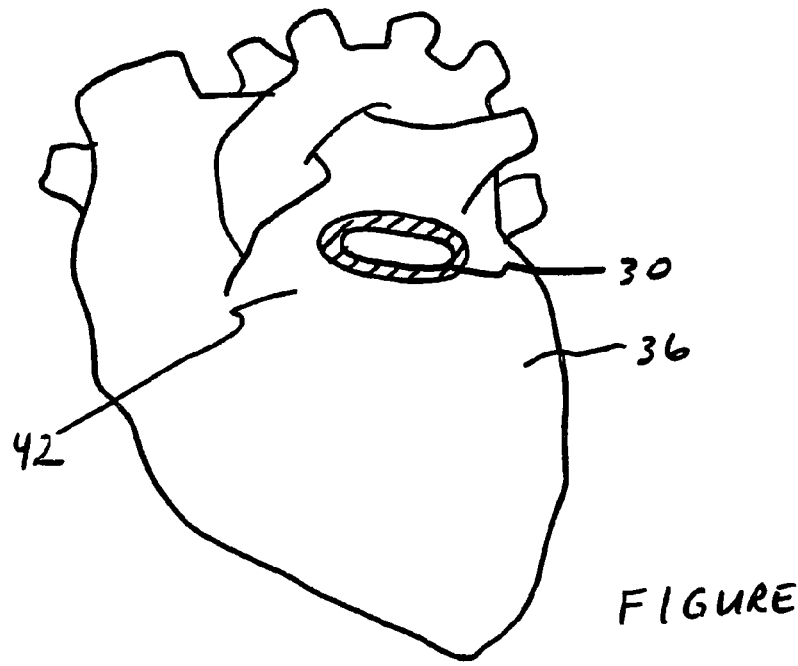
FIG. 12D illustrates a perspective view of an embodiment of an implanted device in accordance with the present invention.
Figure 12B:
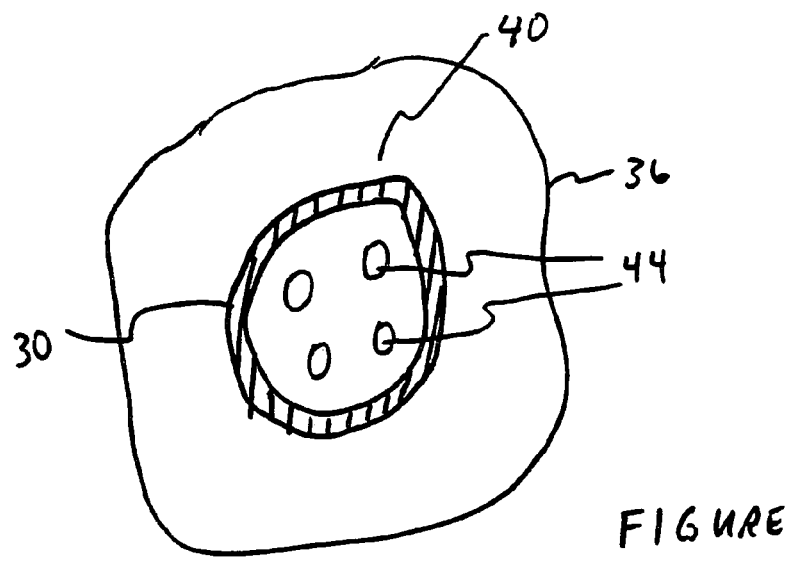
Figure 12E:
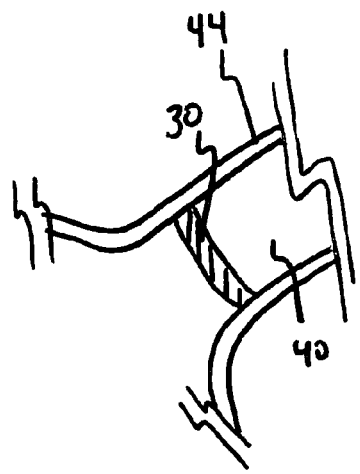
FIG. 12E illustrates a section view of an embodiment of a device implanted on an internal surface of a vessel in accordance with the present invention.
Figure 12F:
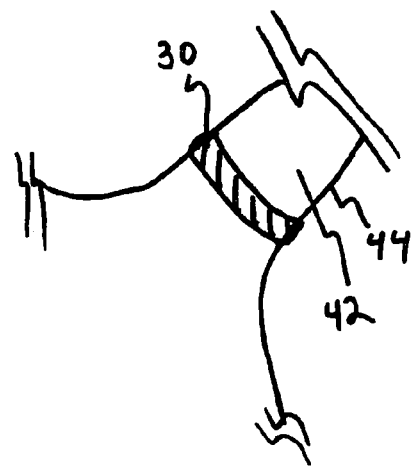
FIG. 12F illustrates a perspective view of an embodiment of a device implanted on an external surface of a vessel in accordance with the present invention.
Figure 12C:
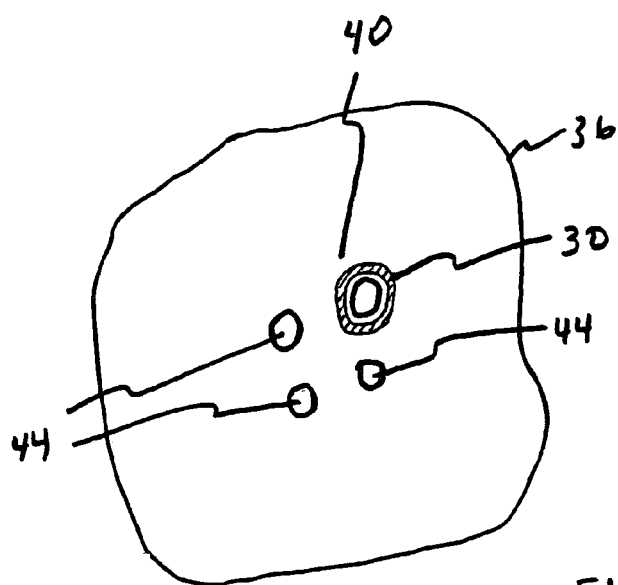
Figure 12G:
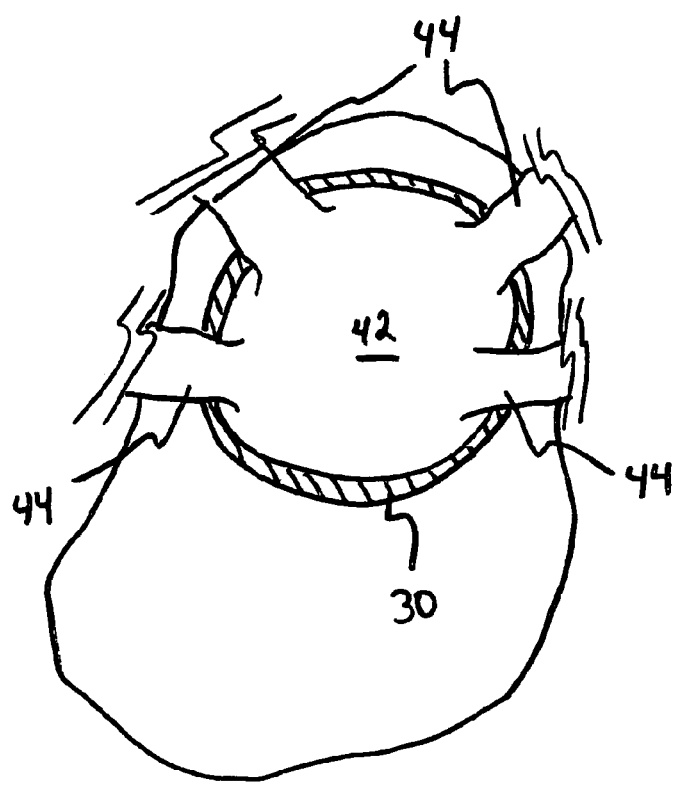
FIG. 12G illustrates a perspective view of an embodiment of an implanted device in accordance with the present invention.

The device 30 is then positioned to contact the tissue 36 and surround that portion of muscle from which the arrhythmia originates. For example, the device 30 may be located on a portion of either an endocardial 40 or epicardial 42 surface of an atrium, ventricle or vessel (such as a pulmonary vein), shown in FIGS. 12A, 12B, 12C and 12D. Alternatively, as illustrated in FIGS. 12E, 12F and 12G, the device 30 may be positioned to surround one or more of the pulmonary veins 44 on either an endocardial 40 or epicardial 42 surface of the heart. As another example, the device 30 may be placed on an internal surface or an external surface of a pulmonary vein 44. The metallic nature of the device 30 together with its tissue-contacting characteristics create a block thereby preventing conduction of the impulse beyond the confines of the device 30 and, ultimately, short-circuiting the arrhythmia In another embodiment of the invention, one or more biologics, drugs or other chemicals/agents may also be included with the device 30. The chemical may be bound, for example, to at least a portion of the surface and/or interior of the elongate members 32 and/or grasping members 34 of the device 30. For example, the grasping members 32 may be hollow allowing the chemical to elute from the hollow area of the grasping members 34 and into the tissue 36. Alternatively, if the device 30 is fabricated from porous materials (as discussed above), the chemical may be contained within and released from the pores and into the tissue 36.

During use, the chemical/agent is released into the myocardial tissue 36 or simply interfaces with the tissue 36 as it contacts the device 30. In an alternate embodiment, the chemical, which may be a coating that is bioabsorbable (or biostable), dissolves or erodes and disappears over time. In yet another embodiment, the chemical promotes formation of an endothelial lining and, eventually, a neointimal layer, thereby encasing the device within the tissue. Alternatively, the chemical may be an anti thrombotic material that functions to prevent clot formation and/or embolization from the implanted device 30.

As a result, the chemical may depress or prevent conduction of aberrant impulses, affect the electrophysiology of the heart to maintain normal sinus rhythm, act as a therapeutic agent, terminate arrhythmias or induce other desired tissue and system responses. Examples of these chemicals/agents include, but are not limited to, blood, copper, zinc, nickel, polylactic acid, polyglycolic acid, heparin, platelet glycoprotein IIb/IIa inhibiting agent, tetracycline, lidocaine, starch, paclitaxel, adriamycin, alcohol fibrosis inducing agents, inflammatory inducing agents, anticoagulants, polymers, drug-eluting polymers, macrophage chemoattractant protein, chemoattractants, therapeutic drugs and other agents/chemicals.

In addition to providing an effective means of treating arrhythmias, the device 30 and methods of use of the present invention effectively reduce pain, infections and postoperative hospital stays. Further, the various treatment methods also improve the quality of life for patients.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating cardiac arrhythmias comprising:
   delivering a treatment device to a target site having a diameter, said treatment device being an implantable stent;
   manipulating said device to conform a shape of said device to a shape of said target site;
   overstretching said diameter of said target site into an overstretched state through expansion of said treatment device and thereby securing said device in place at said target site;
   said overstretching inducing fibrosis in tissue at said target site that results in electrically decoupling said tissue
   said treatment device substantially maintaining said diameter of said target site in said overstretched state and,
   leaving said treatment device implanted at said target site;
   wherein delivering a treatment device to a target site includes delivering said device to an ostium of a pulmonary vein.

2. A method as set forth in claim 1, wherein delivering a treatment device to a target site includes delivering said device to a pulmonary vein.

3. A method as set forth in claim 1, wherein manipulating said device further conforms said target site to said shape of said device, bringing said ostium into a lumen of said device.

4. A method as set forth in claim 1, wherein delivering a treatment device to a target site includes delivering said device to a left atrium.

5. A method as set forth in claim 1, further comprising introducing a bioactive agent to said target site.

6. A method as set forth in claim 5, wherein said bioactive agent comprises a metallic coating.

7. A method of inducing a material tissue response at a target site comprising:
   delivering an implant to said target site having a diameter;
   overstretching said diameter of said target site to an overstretched state by expanding a treatment component of said implant;
   said overstretching exerting a controlled tension of wall tissue of said target site so as to induce a controlled fibrosis at said target site that causes electrical decoupling of said tissue;
   said overstretching also securing said implant in place at said target site;
   said implant substantially maintaining said diameter of said target site in said overstretched state; and,
   leaving said implant at said target site;
   wherein an electrical decoupling resulting in the elimination of cardiac arrhythmias is achieved; and;
   wherein delivering a treatment device to a target site includes delivery to a region that at least includes a pulmonary ostium.

8. A method according to claim 7, wherein said overstretching includes ensuring contact of a drug with said tissue.

* * * * *